(12) United States Patent
Sun et al.

(10) Patent No.: US 9,409,943 B2
(45) Date of Patent: Aug. 9, 2016

(54) HEPATITIS C VIRUS INHIBITORS

(71) Applicant: Bristol-Myers Squibb Company, Princeton, NJ (US)

(72) Inventors: Li-Qiang Sun, Glastonbury, CT (US); Qian Zhao, Wallingford, CT (US); Paul Michael Scola, Glastonbury, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/436,835

(22) PCT Filed: Oct. 31, 2013

(86) PCT No.: PCT/US2013/067665
§ 371 (c)(1),
(2) Date: Apr. 17, 2015

(87) PCT Pub. No.: WO2014/070974
PCT Pub. Date: May 8, 2014

(65) Prior Publication Data
US 2015/0239930 A1  Aug. 27, 2015

Related U.S. Application Data

(60) Provisional application No. 61/722,317, filed on Nov. 5, 2012.

(51) Int. Cl.
| C07D 487/04 | (2006.01) |
| C07K 5/083 | (2006.01) |
| A61K 38/20 | (2006.01) |
| A61K 38/21 | (2006.01) |
| A61K 45/06 | (2006.01) |
| A61K 31/7056 | (2006.01) |
| A61K 31/407 | (2006.01) |
| A61K 38/06 | (2006.01) |

(52) U.S. Cl.
CPC .......... *C07K 5/0804* (2013.01); *A61K 31/407* (2013.01); *A61K 31/7056* (2013.01); *A61K 38/06* (2013.01); *A61K 38/20* (2013.01); *A61K 38/21* (2013.01); *A61K 45/06* (2013.01)

(58) Field of Classification Search
None
See application file for complete search history.

(56) References Cited

U.S. PATENT DOCUMENTS

| 5,223,432 | A | 6/1993 | Wirz et al. |
| 7,449,479 | B2 | 11/2008 | Wang et al. |
| 7,582,605 | B2 | 9/2009 | Moore et al. |
| 7,601,709 | B2 | 10/2009 | Miao et al. |
| 7,605,126 | B2 | 10/2009 | Niu et al. |
| 7,635,683 | B2 | 12/2009 | Gai et al. |
| 7,915,291 | B2 | 3/2011 | Wang et al. |
| 8,232,246 | B2 | 7/2012 | McDaniel et al. |
| 8,268,776 | B2 | 9/2012 | Sun et al. |
| 8,299,094 | B2 | 10/2012 | Wang et al. |
| 8,309,685 | B2 | 11/2012 | Petter et al. |
| 8,338,606 | B2 | 12/2012 | Perrone et al. |
| 8,415,374 | B2 | 4/2013 | Lemm et al. |
| 8,507,722 | B2 | 8/2013 | Wang |
| 8,710,229 | B2 | 4/2014 | Wang et al. |
| 8,957,203 | B2 * | 2/2015 | Hiebert ................ C07D 487/04 540/450 |
| 2005/0209135 | A1 | 9/2005 | Busacca et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0279821 | A1 | 11/2008 | Niu et al. |

(Continued)

FOREIGN PATENT DOCUMENTS

| WO | WO 98/17679 A1 | 4/1998 |
| WO | WO 98/22106 A1 | 5/1998 |
| WO | WO 99/07733 A2 | 2/1999 |

(Continued)

OTHER PUBLICATIONS

Eley, T. et al., "Improved Bioavailability and Mitigated Food Effect for Asunaprevir (ASV) Utilizing a Lipid-Based Formulation: Similar Exposure with 100mg Bid Softgel Capsule (SGC) Relative to 200mg BID of Phase 2 Tablet", Abstract No. A-1247, Interscience Conference on Antimicrobial Agents and Chemotherapy, (Sep. 12, 2012).

(Continued)

*Primary Examiner* — Thomas S Heard
(74) *Attorney, Agent, or Firm* — Pamela A. Mingo

(57) ABSTRACT

Hepatitis C virus inhibitors having the general formula (I) are disclosed. Compositions comprising the compounds and methods for using the compounds to inhibit HCV are also disclosed.

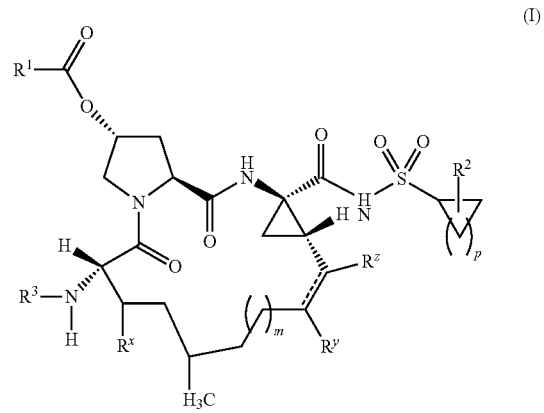

20 Claims, No Drawings

(56) References Cited

U.S. PATENT DOCUMENTS

| | | |
|---|---|---|
| 2013/0302414 A1 | 11/2013 | Perrone |
| 2014/0235617 A1 | 8/2014 | Gao et al. |

FOREIGN PATENT DOCUMENTS

| | | | |
|---|---|---|---|
| WO | WO 99/07734 | A2 | 2/1999 |
| WO | WO 00/09543 | A2 | 2/2000 |
| WO | WO 00/09558 | A1 | 2/2000 |
| WO | WO 00/59929 | A1 | 10/2000 |
| WO | WO 02/08244 | A2 | 1/2002 |
| WO | WO 02/060926 | A2 | 8/2002 |
| WO | WO 03/053349 | A2 | 7/2003 |
| WO | WO 03/062265 | A2 | 7/2003 |
| WO | WO 03/064416 | A1 | 8/2003 |
| WO | WO 03/064455 | A2 | 8/2003 |
| WO | WO 03/064456 | A1 | 8/2003 |
| WO | WO 03/066103 | A1 | 8/2003 |
| WO | WO 03/099274 | A1 | 12/2003 |
| WO | WO 03/099316 | A1 | 12/2003 |
| WO | WO 2004/009121 | A1 | 1/2004 |
| WO | WO 2004/032827 | A2 | 4/2004 |
| WO | WO 2004/037855 | A1 | 5/2004 |
| WO | WO 2004/043339 | A2 | 8/2004 |
| WO | WO 2004/072243 | A2 | 11/2004 |
| WO | WO 2004/093798 | A2 | 11/2004 |
| WO | WO 2004/093915 | A1 | 11/2004 |
| WO | WO 2004/094452 | A2 | 11/2004 |
| WO | WO 2004/101602 | A2 | 11/2004 |
| WO | WO 2004/101605 | A1 | 11/2004 |
| WO | WO 2004/103996 | A1 | 12/2004 |
| WO | WO 2004/113365 | A2 | 12/2004 |
| WO | WO 2005/010029 | A1 | 2/2005 |
| WO | WO 2005/028501 | A1 | 3/2005 |
| WO | WO 2005/037214 | A2 | 4/2005 |
| WO | WO 2005/037860 | A2 | 4/2005 |
| WO | WO 2005/046712 | A1 | 5/2005 |
| WO | WO 2005/051410 | A1 | 6/2005 |
| WO | WO 2005/051980 | A1 | 6/2005 |
| WO | WO 2005/054430 | A2 | 6/2005 |
| WO | WO 2005/070955 | A1 | 8/2005 |
| WO | WO 2005/073216 | A2 | 8/2005 |
| WO | WO 2005/095403 | A2 | 10/2005 |
| WO | WO 2005/116054 | A1 | 12/2005 |
| WO | WO 2006/000085 | A1 | 1/2006 |
| WO | WO 2006/007700 | A1 | 1/2006 |
| WO | WO 2006/007708 | A1 | 1/2006 |
| WO | WO 2006/016930 | A2 | 2/2006 |
| WO | WO 2006/020276 | A2 | 2/2006 |
| WO | WO 2006/026352 | A1 | 3/2006 |
| WO | WO 2006/033878 | A1 | 3/2006 |
| WO | WO 2006/043145 | A1 | 4/2006 |
| WO | WO 2006/086381 | A2 | 8/2006 |
| WO | WO 2006/096652 | A2 | 9/2006 |
| WO | WO 2006/119061 | A2 | 11/2006 |
| WO | WO 2006/122188 | A2 | 11/2006 |
| WO | WO 2006/130552 | A2 | 12/2006 |
| WO | WO 2006/130553 | A2 | 12/2006 |
| WO | WO 2006/130554 | A2 | 12/2006 |
| WO | WO 2006/130607 | A2 | 12/2006 |
| WO | WO 2006/130626 | A2 | 12/2006 |
| WO | WO 2006/130627 | A2 | 12/2006 |
| WO | WO 2006/130628 | A2 | 12/2006 |
| WO | WO 2006/130666 | A2 | 12/2006 |
| WO | WO 2006/130686 | A2 | 12/2006 |
| WO | WO 2006/130687 | A2 | 12/2006 |
| WO | WO 2006/130688 | A2 | 12/2006 |
| WO | WO 2007/001406 | A2 | 1/2007 |
| WO | WO 2007/008657 | A2 | 1/2007 |
| WO | WO 2007/009109 | A2 | 1/2007 |
| WO | WO 2007/009227 | A1 | 1/2007 |
| WO | WO 2007/011658 | A1 | 1/2007 |
| WO | WO 2007/014918 | A1 | 2/2007 |
| WO | WO 2007/014919 | A1 | 2/2007 |
| WO | WO 2007/014920 | A1 | 2/2007 |
| WO | WO 2007/014921 | A1 | 2/2007 |
| WO | WO 2007/014922 | A1 | 2/2007 |
| WO | WO 2007/014923 | A1 | 2/2007 |
| WO | WO 2007/014924 | A1 | 2/2007 |
| WO | WO 2007/014925 | A1 | 2/2007 |
| WO | WO 2007/014926 | A1 | 2/2007 |
| WO | WO 2007/014927 | A2 | 2/2007 |
| WO | WO 2007/015787 | A1 | 2/2007 |
| WO | WO 2007/015824 | A2 | 2/2007 |
| WO | WO 2007/015855 | A1 | 2/2007 |
| WO | WO 2007/016441 | A1 | 2/2007 |
| WO | WO 2007/016476 | A2 | 2/2007 |
| WO | WO 2007/017144 | A2 | 2/2007 |
| WO | WO 2007/025307 | A2 | 3/2007 |
| WO | WO 2007/030656 | A1 | 3/2007 |
| WO | WO 2007/044893 | A2 | 4/2007 |
| WO | WO 2007/044933 | A1 | 4/2007 |
| WO | WO 2007/056120 | A1 | 5/2007 |
| WO | WO 2007/082131 | A1 | 7/2007 |
| WO | WO 2007/106317 | A2 | 9/2007 |
| WO | WO 2007/120595 | A2 | 10/2007 |
| WO | WO 2007/131966 | A1 | 11/2007 |
| WO | WO 2007/143694 | A2 | 12/2007 |
| WO | WO 2007/148135 | A1 | 12/2007 |
| WO | WO 2008/002924 | A2 | 1/2008 |
| WO | WO 2008/005511 | A2 | 1/2008 |
| WO | WO 2008/005565 | A2 | 1/2008 |
| WO | WO 2008/008502 | A1 | 1/2008 |
| WO | WO 2008/008776 | A2 | 1/2008 |
| WO | WO 2008/019266 | A2 | 2/2008 |
| WO | WO 2008/019289 | A2 | 2/2008 |
| WO | WO 2008/019303 | A2 | 2/2008 |
| WO | WO 2008/021733 | A2 | 2/2008 |
| WO | WO 2008/021871 | A2 | 2/2008 |
| WO | WO 2008/021956 | A2 | 2/2008 |
| WO | WO 2008/021960 | A2 | 2/2008 |
| WO | WO 2008/022006 | A2 | 2/2008 |
| WO | WO 2008/051475 | A2 | 5/2008 |
| WO | WO 2008/051477 | A2 | 5/2008 |
| WO | WO 2008/051514 | A2 | 5/2008 |
| WO | WO 2008/057208 | A2 | 5/2008 |
| WO | WO 2008/057209 | A1 | 5/2008 |
| WO | WO 2008/057871 | A2 | 5/2008 |
| WO | WO 2008/057873 | A2 | 5/2008 |
| WO | WO 2008/057875 | A2 | 5/2008 |
| WO | WO 2008/057995 | A2 | 5/2008 |
| WO | WO 2008/059046 | A1 | 5/2008 |
| WO | WO 2008/060927 | A2 | 5/2008 |
| WO | WO 2008/064057 | A1 | 5/2008 |
| WO | WO 2008/064061 | A1 | 5/2008 |
| WO | WO 2008/064066 | A1 | 5/2008 |
| WO | WO 2008/070358 | A2 | 6/2008 |
| WO | WO 2008/086161 | A1 | 7/2008 |
| WO | WO 2008/092954 | A2 | 8/2008 |
| WO | WO 2008/092955 | A1 | 8/2008 |
| WO | WO 2008/095058 | A1 | 8/2008 |
| WO | WO 2008/095999 | A1 | 8/2008 |
| WO | WO 2008/096001 | A1 | 8/2008 |
| WO | WO 2008/096002 | A1 | 8/2008 |
| WO | WO 2008/098368 | A1 | 8/2008 |
| WO | WO 2008/101665 | A1 | 8/2008 |
| WO | WO 2008/106130 | A2 | 9/2008 |
| WO | WO 2008/128921 | A1 | 10/2008 |
| WO | WO 2008/134395 | A1 | 11/2008 |
| WO | WO 2008/134397 | A1 | 11/2008 |
| WO | WO 2008/134398 | A1 | 11/2008 |
| WO | WO 2008/137779 | A2 | 11/2008 |
| WO | WO 2008/141227 | A1 | 11/2008 |
| WO | WO 2009/005676 | A2 | 1/2009 |
| WO | WO 2009/005677 | A2 | 1/2009 |
| WO | WO 2009/005690 | A2 | 1/2009 |
| WO | WO 2009/010804 | A1 | 1/2009 |
| WO | WO 2009/014730 | A1 | 1/2009 |
| WO | WO 2009/047264 | A1 | 4/2009 |
| WO | WO 2009/053828 | A2 | 4/2009 |
| WO | WO 2009/055335 | A2 | 4/2009 |
| WO | WO 2009/064955 | A1 | 5/2009 |
| WO | WO 2009/064975 | A1 | 5/2009 |
| WO | WO 2009/070689 | A1 | 6/2009 |

(56) References Cited

FOREIGN PATENT DOCUMENTS

| | | |
|---|---|---|
| WO | WO 2009/070692 A1 | 6/2009 |
| WO | WO 2009/073713 A1 | 6/2009 |
| WO | WO 2009/073719 A1 | 6/2009 |
| WO | WO 2009/073780 A1 | 6/2009 |
| WO | WO 2009/076166 A2 | 6/2009 |
| WO | WO 2009/076173 A2 | 6/2009 |
| WO | WO 2009/079352 A1 | 6/2009 |
| WO | WO 2009/079353 A1 | 6/2009 |
| WO | WO 2009/080542 A1 | 7/2009 |
| WO | WO 2009/082697 A1 | 7/2009 |
| WO | WO 2009/082701 A1 | 7/2009 |
| WO | WO 2009/085659 A1 | 7/2009 |
| WO | WO 2009/094438 A1 | 7/2009 |
| WO | WO 2009/094443 A1 | 7/2009 |
| WO | WO 2009/108507 A1 | 9/2009 |
| WO | WO 2009/117594 A1 | 9/2009 |
| WO | WO 2009/129109 A1 | 10/2009 |
| WO | WO 2009/134624 A1 | 11/2009 |
| WO | WO 2009/134987 A1 | 11/2009 |
| WO | WO 2009/139792 A1 | 11/2009 |
| WO | WO 2009/140475 A1 | 11/2009 |
| WO | WO 2009/140500 A1 | 11/2009 |
| WO | WO 2009/142842 A2 | 11/2009 |
| WO | WO 2009/146347 A1 | 12/2009 |
| WO | WO 2009/148923 A1 | 12/2009 |
| WO | WO 2010/011566 A1 | 1/2010 |
| WO | WO 2010/015545 A1 | 2/2010 |
| WO | WO 2010/030359 A2 | 3/2010 |
| WO | WO 2010/031829 A1 | 3/2010 |
| WO | WO 2010/031832 A2 | 3/2010 |
| WO | WO 2010/033466 A1 | 3/2010 |
| WO | WO 2010/034105 A1 | 4/2010 |
| WO | WO 2010/036551 A1 | 4/2010 |
| WO | WO 2010/036871 A1 | 4/2010 |
| WO | WO 2010/036896 A1 | 4/2010 |
| WO | WO 2010/059937 A1 | 5/2010 |
| WO | WO 2010/065577 A1 | 6/2010 |
| WO | WO 2010/068760 A2 | 6/2010 |
| WO | WO 2010/068761 A2 | 6/2010 |
| WO | WO 2010/075127 A1 | 7/2010 |
| WO | WO 2010/077783 A1 | 7/2010 |
| WO | WO 2010/080389 A1 | 7/2010 |
| WO | WO 2010/088394 A1 | 8/2010 |
| WO | WO 2010/115981 A1 | 10/2010 |
| WO | WO 2010/116248 A1 | 10/2010 |
| WO | WO 2010/132163 A1 | 11/2010 |
| WO | WO 2010/145523 A1 | 12/2010 |
| WO | WO 2011/002807 A1 | 1/2011 |
| WO | WO 2011/002808 A1 | 1/2011 |
| WO | WO 2011/005646 A2 | 1/2011 |
| WO | WO 2011/014487 A1 | 2/2011 |
| WO | WO 2011/025849 A1 | 3/2011 |
| WO | WO 2011/034518 A1 | 3/2011 |
| WO | WO 2011/038283 A1 | 3/2011 |
| WO | WO 2011/038293 A1 | 3/2011 |
| WO | WO 2011/041551 A1 | 4/2011 |
| WO | WO 2011/046811 A1 | 4/2011 |
| WO | WO 2011/049908 A2 | 4/2011 |
| WO | WO 2011/063501 A1 | 6/2011 |
| WO | WO 2011/063502 A1 | 6/2011 |
| WO | WO 2011/072370 A1 | 6/2011 |
| WO | WO 2011/091757 A1 | 8/2011 |
| WO | WO 2011/112558 A2 | 9/2011 |
| WO | WO 2011/150190 A2 | 12/2011 |
| WO | WO 2011/156337 A2 | 12/2011 |
| WO | WO 2012/018829 A1 | 2/2012 |
| WO | WO 2012/019299 A1 | 2/2012 |
| WO | WO 2012/037259 A1 | 3/2012 |
| WO | WO 2012/040040 A1 | 3/2012 |
| WO | WO 2012/040167 A1 | 3/2012 |
| WO | WO 2012/040242 A1 | 3/2012 |
| WO | WO 2012/047764 A1 | 4/2012 |
| WO | WO 2012/054874 A1 | 4/2012 |
| WO | WO 2012/082672 A2 | 6/2012 |
| WO | WO 2012/092409 A2 | 7/2012 |
| WO | WO 2012/092411 A2 | 7/2012 |
| WO | WO 2012/151195 A1 | 11/2012 |
| WO | WO 2012/166459 A1 | 12/2012 |
| WO | WO 2012/173983 A1 | 12/2012 |
| WO | WO 2013/028465 A1 | 2/2013 |
| WO | WO 2013/028470 A1 | 2/2013 |
| WO | WO 2013/028471 A1 | 2/2013 |
| WO | WO 2013/040568 A1 | 3/2013 |
| WO | WO 2013/066753 A1 | 5/2013 |
| WO | WO 2013/074386 A2 | 5/2013 |
| WO | WO 2013/106689 A1 | 7/2013 |
| WO | WO 2013/120371 A1 | 8/2013 |
| WO | WO 2014/008285 A1 | 1/2014 |
| WO | WO 2014/019344 A1 | 2/2014 |
| WO | WO 2014/025736 A1 | 2/2014 |
| WO | WO 2014/062196 A1 | 4/2014 |
| WO | WO 2014/070964 A1 | 5/2014 |
| WO | WO 2014/071007 A1 | 5/2014 |
| WO | WO 2014/071032 A1 | 5/2014 |
| WO | WO 2014/137869 A1 | 9/2014 |

OTHER PUBLICATIONS

Lauer, G.M. et al., "Hepatitis C Virus Infection", The New England Journal of Medicine, vol. 345, No. 1, pp. 41-52 (2001).

Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S. et al., "Chemoenzymatic Synthesis of (R)-(—)-Citramalic Acid", Synthesis, pp. 365-366 (1992).

* cited by examiner

HEPATITIS C VIRUS INHIBITORS

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In a first aspect the present disclosure provides a compound of formula (I)

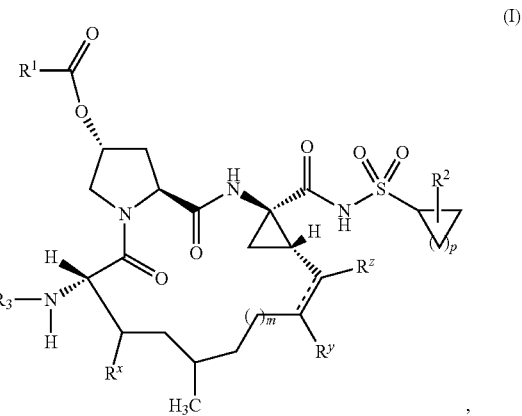

or a pharmaceutically acceptable salt thereof, wherein p is 1 or 2;

$\text{-----}$ is a single or double bond;

$R^1$ is selected from aryl and $-NR^qR^{q'}$, wherein $R^q$ and $R^{q'}$ are independently selected from hydrogen, alkyl, and phenyl wherein the phenyl is optionally fused to a five- or six-membered heterocyclic ring containing two oxygen atoms and wherein the phenyl is optionally substituted with one, two, or three groups independently selected from alkoxy, alkyl, halo, and haloalkyl; or, wherein $R^q$ and $R^{q'}$, together with the nitrogen atom to which they are attached, form a five membered ring optionally fused to a phenyl ring, wherein the phenyl ring is optionally substituted with one, two, or three groups independently selected from alkoxy, alkyl, halo, and haloalkyl;

$R^x$ is selected from methyl and ethyl;

$R^y$ and $R^z$ are independently selected from hydrogen and hydroxy; provided that when $\text{-----}$ is a double bond, $R^y$ and $R^z$ are each hydrogen;

$R^2$ is selected from hydrogen, alkyl, halo, haloalkoxy, haloalkyl, and hydroxyalkyl; and $R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl.

In a first embodiment of the first aspect the present disclosure provides a compound of formula (I), or a pharmaceutically acceptable salt thereof, wherein m is 1. In a second embodiment $\text{-----}$ is a double bond.

In a third embodiment of the first aspect the present disclosure provides a compound of formula (I), or a pharmaceutically acceptable salt thereof, wherein p is 1.

In a fourth embodiment of the first aspect the present disclosure provides a compound of formula (I), or a pharmaceutically acceptable salt thereof, wherein $R^2$ is selected from alkyl and haloalkyl.

In a fifth embodiment of the first aspect the present disclosure provides a compound of formula (I), or a pharmaceutically acceptable salt thereof, wherein $R^3$ is selected from alkoxycarbony and haloalkoxycarbonyl.

In a sixth embodiment of the first aspect the present disclosure provides a compound of formula (I), or a pharmaceutically acceptable salt thereof, wherein:

m is 1,

----- is a double bond;

p is 1;

$R^2$ is selected from alkyl and haloalkyl; and $R^3$ is selected from alkoxycarbony and haloalkoxycarbonyl.

In a second aspect the present disclosure provides a composition comprising a compound of formula (I), or a pharmaceutically acceptable salt thereof, and a pharmaceutically acceptable carrier. In a first embodiment of the second aspect the present disclosure provides a composition comprising a compound of formula (I), or a pharmaceutically acceptable salt thereof, at least one additional compound having anti-HCV activity, and a pharmaceutical carrier. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is selected from interleukin 2, interleukin 6, interleukin 12, Imiquimod, ribavirin, an inosine 5'-monophosphate dehydrogenase inhibitor, amantadine, and rimantadine. In a fifth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of formula (I), or a pharmaceutically acceptable salt thereof. In a first embodiment of the third aspect the method further comprises administering at least one additional compound having anti-HCV activity prior to, after, or simultaneously with the compound of formula (I), or a pharmaceutically acceptable salt thereof. In a second embodiment of the third aspect at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, Imiquimod, ribavirin, an inosine 5'-monophosphate dehydrogenase inhibitor, amantadine, and rimantadine. In a fifth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substitutent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxycarbonyl," as used herein, refers to an alkoxyalkoxy group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms. In one embodiment the hydrocarbon chain has from one to six atoms. In another embodiment the hydrocarbon chain has from one to four atoms.

The term "alkylamino," as used herein, refers to —NHR, wherein R is an alkyl group.

The term "alkylaminocarbonyl," as used herein, refers to an alkylamino group attached to the parent molecular moiety through a carbonyl group.

The term "alkylcarbonyl," as used herein, refers to an alkyl group attached to the parent molecular moiety through a carbonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indanyl, indenyl, naphthyl, phenyl, and tetrahydronaphthyl. In one embodiment the aryl is a phenyl group.

The term "carbonyl," as used herein, refers to —C(O)—.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "cycloalkylalkoxy," as used herein, refers to a (cycloalkyl)alkyl group attached to the parent molecular moiety through an oxygen atom.

The term "cycloalkylalkoxycarbonyl," as used herein, refers to a cycloalkylalkoxy group attached to the parent molecular moiety through a carbonyl group.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "deuteroalkoxycarbonyl," as used herein, refers to an alkoxycarbonyl group wherein one or more of the hydrogen atoms are replaced by deuterium atoms.

The term "deuterohaloalkoxycarbonyl," as used herein, refers to a haloalkoxycarbonyl group wherein one or more of the hydrogen atoms are replaced by deuterium atoms.

The term "dialkylamino," as used herein, refers to —NR$^p$R$^q$, wherein R$^p$ and R$^q$ are alkyl groups. The alkyl groups may be the same or different.

The term "dialkylaminocarbonyl," as used herein, refers to a dialkylamino group attached to the parent molecular moiety through a carbonyl group.

The term "dialkylaminocarbonylcarbonyl," as used herein, refers to a dialkylaminocarbonyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylamino," as used herein, refers to an alkyl amino group wherein the alkyl is substituted with one, two, three, or four halogen atoms.

The term "haloalkylaminocarbonyl," as used herein, refers to a haloalkylamino group attached to the parent molecular moiety through a carbonyl group.

The term "haloalkylcarbonyl," as used herein, refers to a haloalkyl group attached to the parent molecular moiety through a carbonyl group.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl. In one embodiment the heteroaryl is selected from pyrazine, pyrazole, pyridine, and thiazole.

The term "heterocyclyl," as used herein, refers to a cyclic, non-aromatic, saturated or partially unsaturated five-, six-, or seven-membered ring where at least one atom is selected from oxygen, nitrogen, and sulfur. The term "heterocyclyl" also includes bicyclic systems where a heterocyclyl ring is fused to a four- to six-membered aromatic or non-aromatic carbocyclic ring or a four- to six-membered non-aromatic ring containing zero, one, or two additional heteratoms selected from nitrogen, oxygen, and sulfur. The heterocyclyl groups of the invention are attached to the parent molecular group through any substitutable carbon or nitrogen atom in the group. Representative examples of heterocyclyl groups include, but are not limited to, benzodioxolyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, and thiomorpholinyl. In one embodiment the heterocycle is tetrahydropyranyl.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "phenyloxycarbonyl," as used herein, refers to a phenyloxy group attached to the parent molecular moiety through a carbonyl group.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

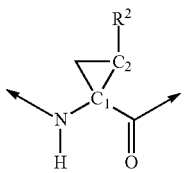

P1 wherein $C_1$ and $C_2$ each represent an asymmetric carbon atom at positions 1 and 2 of the cyclopropyl ring.

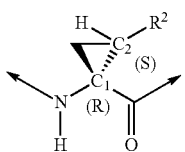

(1R, 2S)

$R^2$ is syn to carbonyl

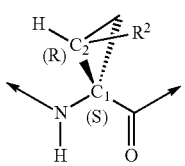

(1S, 2R)

$R^2$ is syn to carbonyl

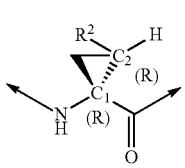

(1R, 2R)

$R^2$ is syn to amide

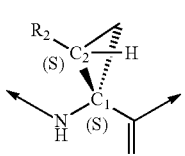

(1S, 2S)

$R^2$ is syn to amide

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immuno-modulator | immune modulator | Maxim Pharmaceuticals Inc., San Diego, CA |
| CellCept | Immuno-suppressant | HCV IgG immuno-suppressant | F. Hoffmann-La Roche LTD, Basel, Switzerland |
| Civacir | Immuno-suppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |

TABLE 1-continued

| Brand Name | Physiological Class | Type of Inhibitor or Target | Source Company |
|---|---|---|---|
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1α | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Bristol-Myers Squibb |
| BMS-984478 | Antiviral | NS5A inhibitor | Bristol-Myers Squibb |
| asunaprevir | Antiviral | serine protease inhibitor | Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: DCM for dichloroethane; DMAP for 4-N,N-dimethylaminopyridine; BOC or Boc for tert-butoxycarbonyl; DMSO for dimethylsulfoxide; BuLi for butyllithium; CDI for 1,1'-carbonyldiimidazole;

DBU for 1,8-diazobicyclo[5.4.0]undec-7-ene; h for hours; min for minutes; rt or RT or Rt for room temperature or retention time (context will dictate); DAST for (diethylamino)sulfur trioxide; DMF for N,N-dimethylformamide; EtOAc for ethyl acetate; DIPEA for diisopropylethylamine; TBME for tert-butyl methyl ether; LiHMDS for lithium hexamethyldisilazide; THF for tetrahydrofuran; MeOH for methanol; HATU for O-(7-azabenzotriazol-1-yl)-N,N,N',N'-tetramethyluronium hexafluorophosphate; DCE for 1,2-dichloroethane; and Et$_3$N or TEA for triethylamine.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Preparation of 1-methylcyclopropane-1-sulfonamide

Scheme:

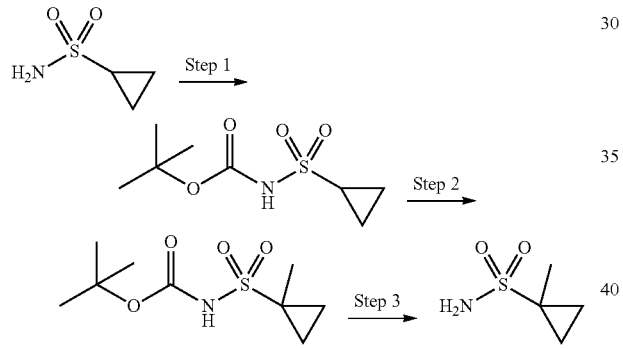

Step 1: Preparation of tert-butyl cyclopropylsulfonylcarbamate

To a solution of cyclopropanesulfonamide (100 g, 82.6 mmol) in DCM (800 ml) was added triethylamine (234 ml, 165 mmol) followed by DMAP (10.28 g, 82.6 mmol) at 0° C. under nitrogen. To this reaction mixture Boc anhydride (247 ml, 107 mmol) in DCM (400 ml) was added slowly. The resulting mixture was stirred for 4 h at room temperature. The reaction mixture was diluted with water and extracted with ethyl acetate. The combine organic layer was washed with 1.5 N HCl solution and 10% NaHCO$_3$ and dried over anhydrous sodium sulfate, filtered and evaporated under reduced pressure to get crude compound (143 g, 65%) as a solid. The crude compound was directly taken for the next step. $^1$H NMR (400 MHz, DMSO-d$_6$): δ ppm 11.08 (s, 1H), 2.90 (m, 1H), 1.48 (s, 9H), 1.06 (m, 4H).

Step 2: Preparation of tert-butyl(1-methylcyclopropyl)sulfonylcarbamate

A solution of tert-butyl cyclopropylsulfonylcarbamate (4.3 g, 20 mmol) was dissolved in dry THF (100 ml) and cooled to −78° C. To this solution was added n-BuLi (17.6 ml, 44 mmol, 2.5 M in hexane) slowly. The reaction mixture was allowed to warm to room temperature over a period of 1.5 h. This mixture was then cooled to −78° C., and a solution of n-BuLi (20 mmol, 8 ml, 2.5M in hexane) was added, stirred for 1 h and a neat solution of methyl iodide (5.68 g, 40 mmol) was added. The reaction mixture was allowed to warm to room temperature with stirring overnight; then was quenched with aqueous saturated NH$_4$Cl (100 ml) at room temperature. The mixture was extracted with EtOAc (100 ml). The organic layer was washed with brine; dried over Na$_2$SO$_4$, filtered and concentrated under reduced pressure to give a yellow oil which was crystallized from hexane to afford the product as a slightly yellow solid (3.1 g, 81%). $^1$H NMR (400 MHz, DMSO-d$_6$): δ ppm 10.97 (s, 1H), 1.44 (s, 12H), 1.35-1.33 (m, 2H), 0.93-0.91 (m, 2H).

Step 3: Preparation of 1-methylcyclopropane-1-sulfonamide

A solution of N-tert-butyl-(1-methyl)-cyclopropyl-sulfonamide (1.91 g, 10 mmol) was dissolved in 4M HCl in dioxane (30 ml) and the reaction mixture stirred at rt for 16 h. The solvent was removed in vacuo to give a yellow oil which was crystallized from EtOAc/hexane (1:4, 40 ml) to yield 1-methyl-cyclopropylsulfonamide, as a white solid (1.25 g, 96%). $^1$H NMR (400 MHz, CDCl$_3$): δ ppm 6.73 (s, 2H), 1.43 (s, 3H), 1.14-1.12 (m, 2H), 0.75-0.73 (m, 2H).

Preparation of tert-butyl((1R,2S)-1-(((1-methylcyclopropyl)sulfonyl)carbamoyl)-2-vinylcyclopropyl)carbamate

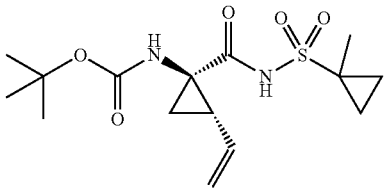 [SMILES: C=C[C@@H]1C[C@]1(NC(=O)OC(C)(C)C)C(=O)NS(=O)(=O)C1(C)CC1]

To a solution of (1R,2S)-1-(tert-butoxycarbonylamino)-2-vinylcyclopropanecarboxylic acid (25 g, 110 mmol) in THF (300 mL) was added CDI (205 g, 127 mmol) and the reaction mass was heated at 85° C. for 1 h. The reaction mass was cooled to rt and to this reaction mass was added 1-methylcyclopropane-1-sulfonamide (17.7 g, 131 mmol) followed by DBU (33.2 mL, 33.5 mmol). The reaction mixture was stirred at rt for 18 h. The solvent was evaporated under reduced pressure and the residue was diluted with water and acidified to pH~2 by using aq. 1.5 N HCl solution. The precipitated solid was isolated via filtration and washed with water to get desired compound (22 g, 58%) as off-white solid. $^1$H NMR (400 MHz, DMSO-d$_6$) δ ppm 11.01-11.17 (m, 1H), 7.17-7.33 (m, 1H), 5.35-5.51 (m, 1H), 5.18-5.29 (m, 1H), 4.99-5.09 (m, 1H), 2.21 (s, 1H), 1.69 (dd, J=7.78, 5.27 Hz, 1H), 1.40 (d, J=3.01 Hz, 14H), 1.20 (dd, J=9.29, 5.27 Hz, 1H), 0.82-0.96 (m, 2H). MS: MS m/z 343 (M⁺+1).

Preparation of (1R,2S)-1-amino-N-((1-methylcyclopropyl)sulfonyl)-2-vinylcyclopropanecarboxamide Hydrochloride

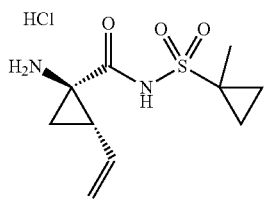 [SMILES: Cl ; C=C[C@@H]1C[C@]1(N)C(=O)NS(=O)(=O)C1(C)CC1]

A solution of tert-butyl((1R,2S)-1-(((1-methylcyclopropyl)sulfonyl)carbamoyl)-2-vinylcyclopropyl)carbamate (40 g, 116 mmol) in 4 N HCl in dioxane (400 mL) was stirred at room temperature for 1 h. The solvent was evaporated under reduced pressure and the residue was washed with diethyl ether to get crude compound (31 g, 95%). The crude compound was used without further purification. ¹H NMR (400 MHz, DMSO-d₆) δ ppm 8.97-9.29 (m, 2H), 5.47-5.66 (m, 1H), 5.32-5.44 (m, 1H), 5.22 (dd, J=10.04, 1.51 Hz, 1H), 2.38 (s, 1H), 2.03 (s, 1H), 1.71 (d, J=3.51 Hz, 1H), 1.46-1.52 (m, 4H), 1.25-1.35 (m, 1H), 0.88-1.01 (m, 2H). MS: MS m/z 245.14 (M⁺+1).

Preparation of (1R,2S)-1-amino-N-((1-(fluoromethyl)cyclopropyl)sulfonyl)-2-vinylcyclopropanecarboxamide Hydrochloride

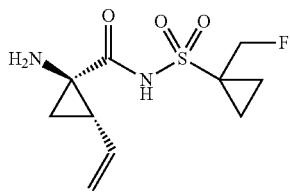 [SMILES: C=C[C@@H]1C[C@]1(N)C(=O)NS(=O)(=O)C1(CF)CC1]

Scheme

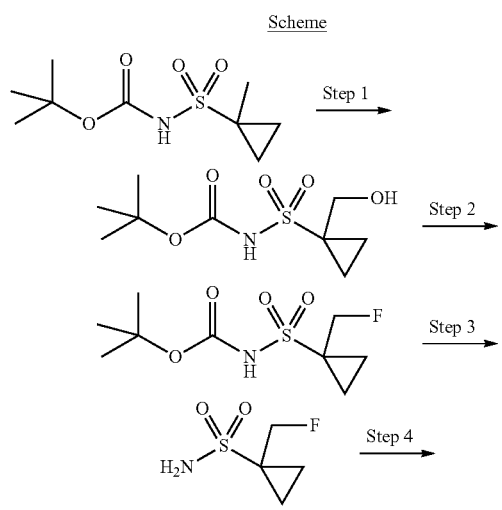

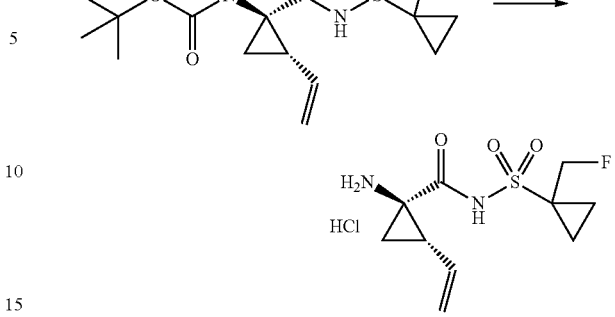

Step 1

To a solution of tert-butyl cyclopropylsulfonylcarbamate (30 g, 136 mmol) in 750 mL of THF was added dropwise butyllithium (1.6 M in hexane, 212 mL, 339 mmol) over 30 min at −78° C. and the resulting mixture was stirred at −78° C. for 1 h. Formaldehyde gas was generated from para-formaldehyde (by heating at 180° C.) and was purged in to the above reaction mass for 30 min at −30° C. The reaction was stirred at the same temperature for 1 h and then allowed to warm to room temperature. The reaction was quenched with aqueous ammonium chloride solution and diluted with water. The resulting mass was washed with ethyl acetate and the aqueous layer was acidified to pH~2 and extracted with ethyl acetate. The combined organics were dried over sodium sulfate and evaporated under reduced pressure to get desired compound tert-butyl(1-(hydroxymethyl)cyclopropyl)sulfonylcarbamate (27 g, 79%) as white solid. ¹H NMR (400 MHz, DMSO-d₆): δ ppm 10.90 (sb, 1H), 4.95 (sb, 1H), 3.75 (s, 2H), 1.42 (s, 9H), 1.27 (m, 2H), 1.08 (m, 2H).

Step 2

A solution of tert-butyl 1-hydroxymethylcyclopropylsulfonylcarbamate (26.0 g, 103 mmol) in DCM (300 mL) was cooled to −78° C. To this solution was added diethylaminosulfur trifluoride ("DAST", 41.0 mL, 310 mmol). The reaction mass was stirred at the same temperature for 30 min. The reaction mass was quenched with aqueous 1N NaOH solution. The organic layer was discarded and the aqueous layer was acidified to pH~2 by using aq. 1.5 N HCl solution. The aqueous solution was extracted with DCM (50 mL×4). The combined organic layers were dried over anhydrous sodium sulfate; filtered; then concentrated to afford desired tert-butyl (1-(fluoromethyl)cyclopropyl)sulfonylcarbamate (19 g, 72%) as gummy solid. ¹H NMR (400 MHz, DMSO-d₆): δ ppm 11.25 (sb, 1H), 4.75 (s, 1H), 4.63 (s, 1H), 1.44 (s, 9H), 1.28 (m, 2H), 1.07 (m, 2H). ¹⁹F NMR: −211.7 (1F).

Step 3

To a solution of tert-butyl 1-fluoromethyl cyclopropylsulfonylcarbamate (19 g, 75 mmol) in dichlormethane (200 mL) at room temperature was added trifluoroacetic acid ("TFA", 50 mL). The reaction mass was stirred at room temperature for 1 h. The solvent was evaporated under reduced pressure and the residue was diluted with hexane. The precipitated solid was isolated via filtration and washed with hexane to afford pure 1-(fluoromethyl)cyclopropane-1-sulfonamide (11 g, 96%) as an off-white solid. $^1$H NMR (400 MHz, DMSO-d$_6$): δ ppm 6.98 (sb, 2H), 4.75 (s, 1H), 4.63 (s, 1H), 1.28 (m, 2H), 1.08 (m, 2H). $^{19}$F NMR: −211.74 (1F).

Step 4

To a solution of (1R,2S)-1-(tert-butoxycarbonylamino)-2-vinylcyclopropanecarboxylic acid (7.5 g, 33 mmol) in DMF (50 mL) was added 1,1'-carbonyldiimidazole ("CDI", 10.7 g, 66.0 mmol) and the reaction mass was heated at 55° C. for 4 h. To this reaction mass was added 1-fluoromethylcyclopropane-1-sulfonamide (6.5 g, 42.9 mmol) followed by 1,8-diazabicyclo[5.4.0]undec-7-ene ("DBU", 6.0 mL, 43 mmol). The reaction mixture was stirred at 55° C. for 18 h. The solvent was evaporated under reduced pressure and the residue was diluted with water and acidified to pH~2 by using aq. 1.5 N HCl solution. The precipitated solid was isolated via filtration and washed with water to afford tert-butyl(1R,2S)-1-(1-(fluoromethyl)cyclopropylsulfonylcarbamoyl)-2-vinylcyclopropylcarbamate as off-white solid (11.5 g, 96%). MS: MS m/z 361.4 (M$^+$−1).

Step 5

A solution of tert-butyl(1R,2S)-1-(1-(fluoromethyl)cyclopropylsulfonylcarbamoyl)-2-vinylcyclopropylcarbamate (11.5 g, 31.7 mmol) in 4 N HCl in dioxane (100 mL) was stirred at room temperature for 1 h. The volatiles were removed under reduced pressure and the residue was washed with diethyl ether to afford crude (1R,2S)-1-amino-N-(1-(fluoromethyl)cyclopropylsulfonyl)-2-vinylcyclopropanecarboxamide hydrochloride (6 g, 72%). The crude compound was taken to the next step without further purification. MS: MS m/z 263.14 (M$^+$+1)

Preparation of 3,3-difluoro-2-methylbutan-2-ylpyridin-2-yl carbonate

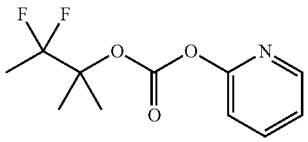 [SMILES: CC(F)(F)C(C)(C)OC(=O)Oc1ccccn1]

Scheme:

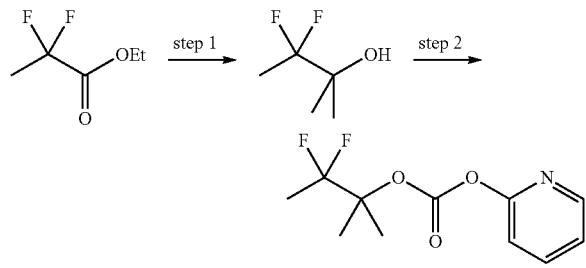

Step 1

Methylmagnesium bromide (24.9 mL, 74.7 mmol) was added dropwise via syringe to a solution of ethyl 2,2-difluoropropanoate (3.44 g, 24.91 mmol) in diethyl ether (50 mL) at −20° C. and stirred at this temp for 1 h before warming up to RT. The reaction was quenched with sat. ammonium chloride and extracted with ether. The organic layer was washed with brine; dried over MgSO$_4$; filtered and concentrated in vauco to afford the crude 3,3-difluoro-2-methylbutan-2-ol (1.84 g, 59.5% yield) as an oil. $^1$H NMR (500 MHz, CDCl$_3$) δ 1.68-1.58 (m, 3H), 1.31 (t, J=1.2 Hz, 6H).

Step 2

To a suspension of sodium hydride, 60% in mineral oil (0.652 g, 16.31 mmol) in THF (25 mL) was added 3,3-difluoro-2-methylbutan-2-ol (1.84 g, 14.82 mmol) at 0° C. After stirring 30 min, the solution was transferred to a solution of di(pyridin-2-yl)carbonate (3.20 g, 14.82 mmol) in THF (25 mL) through a cannula. The formed slurry was stirred at 0° C. for 30 min. The slurry was warmed to rt and stirred for 2 h. The reaction was diluted with EtOAc, washed with brine, dried over MgSO$_4$, filtered, concentrated to give a residue that was purified by silica gel chromatography eluting with 10-50% EtOAc in hexanes to 3,3-difluoro-2-methylbutan-2-yl pyridin-2-yl carbonate (500 mg, 13.76%) as an oil that later crystallized to a white solid upon standing. $^1$H NMR (500 MHz, CDCl$_3$) δ 8.43 (ddd, J=4.9, 2.0, 0.7 Hz, 1H), 7.95-7.75 (m, 1H), 7.31-7.24 (m, 1H), 7.15 (dt, J=8.2, 0.8 Hz, 1H), 1.72 (s, 6H), 1.77-1.66 (m, 3H).

Preparation of pyridin-2-yl(1,1,1-trifluoro-2-methylpropan-2-yl)carbonate

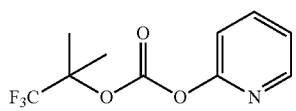 [SMILES: CC(C)(OC(=O)Oc1ccccn1)C(F)(F)F]

To a solution of 1,1,1-trifluoro-2-methylpropan-2-ol (10 g, 78 mmol) in DIPEA (40.9 ml, 234 mmol) was added DMAP (9.54 g, 78 mmol) and the solution was stirred 10 min at room temperature. To the solution was added dipyridin-2-yl carbonate (16.8 g, 78 mmol). The solution was stirred overnight. The reaction mass was filtered, washing with DIPEA (2×10 mL); the filtrate was concentrated under vacuum and then diluted with DCM (300 mL). The solution was washed with aq. 1.5N HCl solution (2×150 mL), followed by brine solution (100 mL). The organic phase was dried over Na$_2$SO$_4$, filtered and concentrated under reduced pressure to afford crude product as red color liquid. The crude compound was purified by silica gel chromatography eluting with EtOAc in pet-ether [0-5% over 25 min] as gradient, using 40 g silica column, collected the product fractions and concentrated to afford pyridin-2-yl(1,1,1-trifluoro-2-methylpropan-2-yl)carbonate (9.0 g, 36 mmol, 46% yield) as colorless liquid. $^1$H NMR (400 MHz, CDCl$_3$) δ ppm 8.41-8.40 (d, J=4.8 Hz, 1H), 7.84-7.79 (m, 1H), 7.28-7.24 (m, 1H), 7.13-7.10 (d, J=10 Hz, 1H), 1.78 (s, 6H). MS: MS m/z 250.54 (M$^+$+1).

Preparation of (3R)-2-((tert-butoxycarbonyl)amino)-3,5-dimethylnon-8-enoic acid

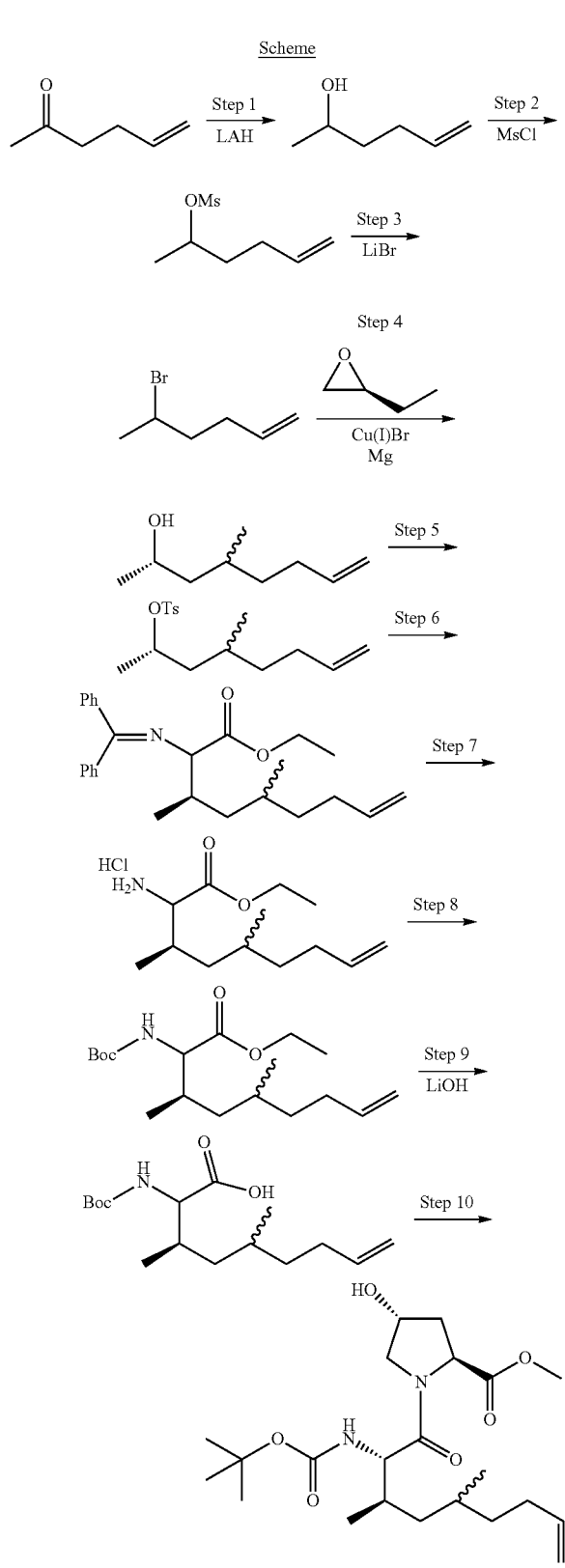

Step 1: Preparation of Hex-5-en-2-ol

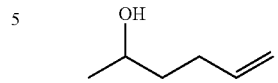

To a solution of lithium aluminum hydride in THF ("LAH", 20.1 g, 106 mmol, 509 mL, 1M solution) was added a solution of hex-5-en-2-one (50 g, 102 mmol) over a period of 30 min. at −20° C. under nitrogen. The reaction mass was allowed to warm to room temperature and stirred for 1 h. The solution was cooled to −20° C. and to it was added aqueous 10% NaOH solution (~100 mL). The organic layer was separated and the aqueous layer was extracted with ether. The combined organics were dried over anhydrous sodium sulfate and concentrated to get crude compound hex-5-en-2-ol as colorless liquid (50 g, 98%). $^1$H NMR (400 MHz, CDCl$_3$): δ ppm 5.87-5.02 (m, 1H), 4.99-4.95 (m, 2H), 3.81-3.83 (m, 1H), 2.17-2.13 (m, 2H), 1.58-1.53 (m, 2H), 1.20-1.19 (d, J=8 Hz, 3H).

Step 2: Preparation of Hex-5-en-2-yl methanesulfonate

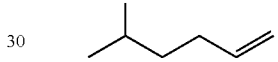

To a solution of hex-5-en-2-ol (50 g crude, 500 mmole) in dichloromethane was added triethylamine (103 m 5 L, 750 mmol) at room temperature. The reaction mass was cooled to 0° C. and to it was added a solution of methane sulfonyl chloride (50.4 mL, 650 mmol) in DCM over a period of 30 min. The reaction mass was allowed to come to room temperature and stirred for 2 h. The solution was washed with water, dried over anhydrous sodium sulfate, filtered and concentrated under reduced pressure to get crude hex-5-en-2-yl methanesulfonate as light brown oil (73 g, 82%). $^1$H NMR (400 MHz, CDCl$_3$): δ ppm 5.84-5.80 (m, 1H), 5.10-5.0 (m, 2H), 4.99-4.98 (m, 1H), 3.15 (s, 3H), 2.52-2.09 (m, 2H), 1.75-1.66 (m, 2H), 1.36-1.34 (d, J=6.4 Hz, 3H).

Step 3: Preparation of 5-bromohex-1-ene

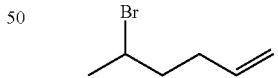

To a solution of hex-5-en-2-yl methanesulfonate (20 g, 0.112 moles) in dry THF (200 mL) was added LiBr (14.6 g, 0.168 moles) portion wise at room temperature over a period of 15 min. The reaction mass was heated at 70° C. for 3 h. The reaction mass was cooled to room temperature and was diluted with water (200 mL). The aqueous solution was extracted with ether (100 mL×3). The combined organics were dried over anhydrous Na2SO4 and concentrated at room temperature. The crude compound was distilled under reduced pressure at 115° C. to afford 5-bromohex-1-ene as colorless liquid (14.5 g, 80%). $^1$H NMR (400 MHz, CDCl$_3$): δ ppm 5.80-5.74 (m, 1H), 5.08-4.98 (m, 2H), 4.14-4.09 (m, 1H), 2.28-2.17 (m, 2H), 1.94-1.81 (m, 2H), 1.71-1.70 (d, J=6.8 Hz, 3H); MS: GC-MS m/z 162.

Step 4: Preparation of (2S)-4-methyloct-7-en-2-ol

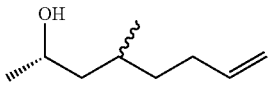 [SMILES: C=CCCC(C)C[C@H](C)OS(=O)(=O)c1ccc(C)cc1]

To magnesium turnings (7.44 g, 0.020 moles) in dry THF (100 mL) and was added iodine (100 mg) at room temperature. To this reaction mass was added a solution of 5-bromohex-1-ene (50.0 g, 362 mmoles) in THF (200 mL). The reaction mass was heated with hot air gun to initiate the reaction. Upon completion of the reaction the solution was transferred by cannula to a solution of (S)-propylene oxide (14 g, 241 mmol) and copper bromide (3.45 g, 24 mmol) in THF (100 mL) at −78° C. The reaction mass was allowed to come to room temperature and was stirred overnight. The reaction mass was quenched with saturated aq. ammonium chloride solution and extracted with diethyl ether (200 mL×3). The combined organic layers were dried over anhydrous $Na_2SO4$; filtered; then concentrated in vacuo at room temperature to get crude compound. The crude compound was purified by column chromatography (Silica gel, 10% TBME in pet ether) to get (2S)-4-methyloct-7-en-2-ol (12.4 g, 30%) as an oil. $^1$H NMR (400 MHz, $CDCl_3$): δ ppm 5.84-5.77 (m, 1H), 5.02-4.92 (m, 2H), 4.05-3.85 (sb, 1H), 2.08-2.06 (m, 2H), 1.29-1.20 (m, 2H), 1.19-1.16 (m, 4H), 0.97-0.87 (m, 6H).

Step 5: Preparation of (2S)-4-methyloct-7-en-2-yl 4-methylbenzenesulfonate

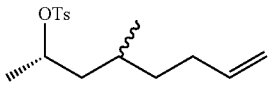

To a solution of (2S)-4-methyloct-7-en-2-ol (39.0 g, 0.274 moles) in pyridine (400 mL) was added 4-(dimethylamino) pyridine ("DMAP", 1.67 g, 0.013 moles) and the solution was stirred for 10 min. p-toluenesulfonyl chloride (60 g, 0.315 moles) was added to the reaction mass at 0° C. The reaction mass was allowed to come to room temperature and stirred overnight. Pyridine was removed under reduced pressure and the residue was diluted with ethyl acetate (200 mL). The organic solution was washed with aqueous 1.5 N HCl solution, saturated aq. Bicarbonate solution, brine solution, dried over anhydrous $Na_2SO_4$, filter, and concentrated under reduced pressure to get crude compound (2S)-4-methyloct-7-en-2-yl 4-methylbenzenesulfonate (54 g, 61%). The crude compound was taken to the next step without further purification.

Step 6: Preparation of (3R)-ethyl 2-((diphenylmethylene)amino)-3,5-dimethylnon-8-enoate

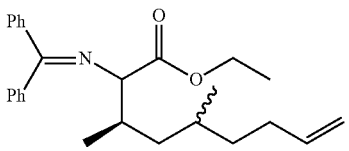 [SMILES: C=CCCC(C)C[C@@H](C)C(N=C(c1ccccc1)c1ccccc1)C(=O)OCC]

To a solution of (2S)-4-methyloct-7-en-2-yl 4-methylbenzenesulfonate (54 g, 0.182 moles) and N-(diphenylmethylene)glycinate ethyl ester (48.7 g, 0.182 moles) in toluene (500 mL) was added LiHMDS (36.5 g, 0.218 moles, 1 M solution in THF) at 0° C. The reaction mass was allowed to come to room temperature and was then heated at 110° C. for 2 h. The reaction mass was cooled to room temperature, quenched with water and extracted with ethyl acetate (200 mL×3). The combined organic layers were dried over anhydrous $Na_2SO_4$, filtered and concentrated under reduced pressure to get crude compound (3R)-ethyl 2-((diphenylmethylene)amino)-3,5-dimethylnon-8-enoate (75 g). The crude compound was taken to the next step without further purification.

Step 7: Preparation of (3R)-ethyl 2-amino-3,5-dimethylnon-8-enoate hydrochloride

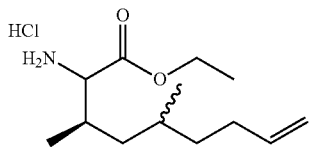 [SMILES: Cl ; C=CCCC(C)C[C@@H](C)C(N)C(=O)OCC]

To a solution of (3R)-ethyl 2-((diphenylmethylene)amino)-3,5-dimethylnon-8-enoate (20 g) in diethyl ether (20 mL) was added aqueous 1.5 N HCl solution (200 mL) and the reaction mass was stirred at room temperature overnight. The reaction mass was washed with diethyl ether (100 mL). The aqueous solution was basified using saturated sodium bicarbonate solution and was extracted with ethyl acetate (100 mL×3). The combined organic layers were dried over anhydrous $Na_2SO_4$, filtered, and concentrated under reduced pressure to get crude compound (3R)-ethyl 2-amino-3,5-dimethylnon-8-enoate hydrochloride (4 g, 30%). The crude compound was taken to the next step without further purification.

Step 8: Preparation of (3R)-ethyl 2-(tert-butoxycarbonylamino)-3,5-dimethylnon-8-enoate

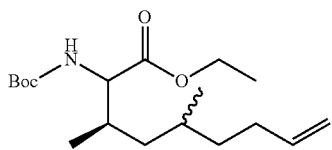 [SMILES: C=CCCC(C)C[C@@H](C)C(NC(=O)OC(C)(C)C)C(=O)OCC]

A solution of (3R)-ethyl 2-amino-3,5-dimethylnon-8-enoate hydrochloride (4 g, 0.017 moles) in DCM (40 mL) was added N,N-diisopropylethylamine ("DIPEA", 3.4 g, 0.026 moles) followed by di-tert-butyl dicarbonate (4.6 g, 0.021 moles) at room temperature. The reaction mass was stirred at room temperature overnight. The reaction mass was diluted with DCM and washed with water. The organic layer was dried over anhydrous $Na_2SO_4$, filtered, and concentrated under reduced pressure to afford the crude compound. The crude compound was purified by column chromatography (Silica gel, 20% ethyl acetate in pet-ether) to get 4.7 g, (94%) of (3R)-ethyl 2-(tert-butoxycarbonylamino)-3,5-dimethyl-non-8-enoate as an oil.

Step 9: Preparation of (3R)-2-(tert-butoxycarbonylamino)-3,5-dimethylnon-8-enoic acid

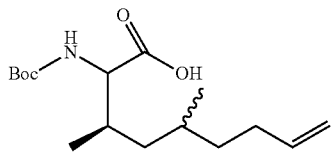 [SMILES: C=CCCC(C)C[C@@H](C)C(NC(=O)OC(C)(C)C)C(=O)O]

To a solution of (3R)-ethyl 2-(tert-butoxycarbonylamino)-3,5-dimethylnon-8-enoate (20 g, 0.061 moles) in THF/water (200 mL, 1:1) was added methanol (60.25 mL) followed by LiOH (7.7 g, 0.183 moles) at room temperature. The reaction mass was stirred at room temperature overnight. The solution was concentrated under reduced pressure and the residue was diluted with water (200 mL). The aqueous solution was acidified with aqueous 1.5 N HCl solution to pH~3 and extracted with ethyl acetate (100 mL×3). The combined organic layers were dried over anhydrous $Na_2SO_4$ and concentrated under reduce pressure to get crude compound. The crude compound was purified by column chromatography (Silica gel, 3% methanol in DCM) to get 12.4 g (68%) of (3R)-2-(tert-butoxycarbonylamino)-3,5-dimethylnon-8-enoic acid as a gummy liquid. $^1H$ NMR (400 MHz, DMSO-$d_6$): δ ppm 12.4 (sb, 1H), 6.92-6.85 (m, 1H), 5.81-5.75 (m, 1H), 5.04-4.93 (m, 2H), 4.12-3.91 (m, 1H), 2.18-1.98 (m, 4H), 1.5 (s, 9H), 1.35-1.02 (m, 3H), 0.98-0.85 (m, 6H).

Step 10: Preparation of (2S,4R)-methyl 1-((3R)-2-((tert-butoxycarbonyl)amino)-3,5-5dimethylnon-8-enoyl)-4-hydroxypyrrolidine-2-carboxylate

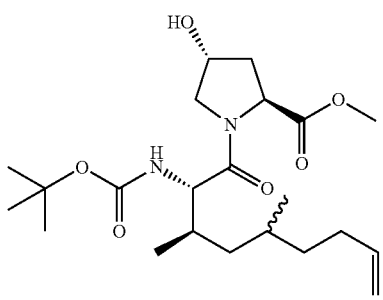 [SMILES: C=CCCC(C)C[C@@H](C)[C@H](NC(=O)OC(C)(C)C)C(=O)N1C[C@H](O)C[C@H]1C(=O)OC]

O-(7-Azabenzotriazol-1-yl)-N,N,N',N'-tetramethyluronium hexafluorophosphate (HATU, 31.7 g, 83 mmol) was added to a solution of (2S,4R)-methyl 4-hydroxypyrrolidine-2-carboxylate HCl (16.68 g, 92 mmol), (3R)-2-((tertbutoxycarbonyl)amino)-3,5-dimethylnon-8-enoic acid (25 g, 83 mmol) and $NEt_3$ (34.9 mL, 250 mmol) in DCM (250 mL) and stirred at RT for 16 h. The reaction was washed with 1N HCl (3×) and then brine. The organics were dried with magnesium sulfate, filtered and concentrated under vacuum. The crude material was purified via silica gel chromatography using 20-60% Acetone in hexanes to give the desired product (2S, 4R)-methyl 1-((2S,3R)-2-((tert-butoxycarbonyl)amino)-3,5-dimethylnon-8-enoyl)-4-hydroxypyrrolidine-2-carboxylate (10.8 g, 30% yield), MS: MS m/z 427.2 ($M^+$+1) and the undesired product (2S,4R)-methyl 1-((2R,3R)-2-((tert-butoxycarbonyl)amino)-3,5-dimethylnon-8-enoyl)-4-hydroxypyrrolidine-2-carboxylate (12 g, 34% yield). MS: MS m/z 427.2 ($M^+$+1).

Preparation of tert-butyl((2R,6S,7R,13aS,14aR,16aS, Z)-2-hydroxy-7,9-dimethyl-14a-(((1-methylcyclopropyl)sulfonyl)carbamoyl)-5,16-dioxo-1,2,3,5,6,7, 8,9,10,11,13a,14,14a,15,16,16a-hexadecahydrocyclopropa[e]pyrrolo[1,2-a][1,4] diazacyclopentadecin-6-yl)carbamate

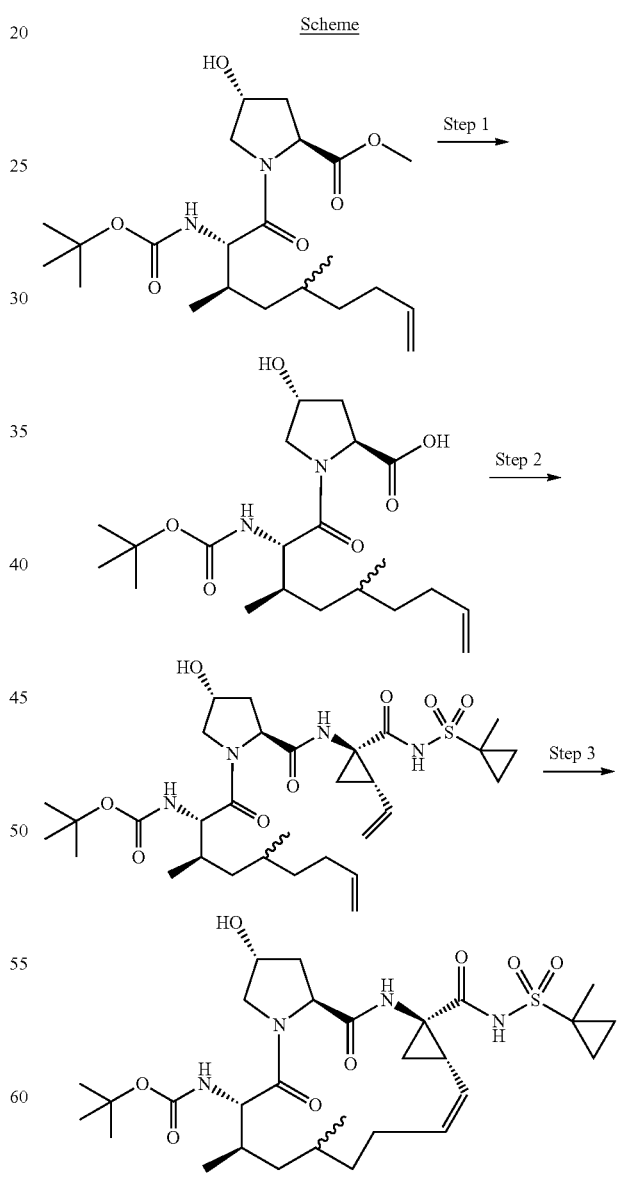

Step 1: Preparation of (2S,4R)-1-(((3R)-2-((tert-bu-toxycarbonyl)amino)-3,5-dimethylnon-8-enoyl)-4-hydroxypyrrolidine-2-carboxylic acid

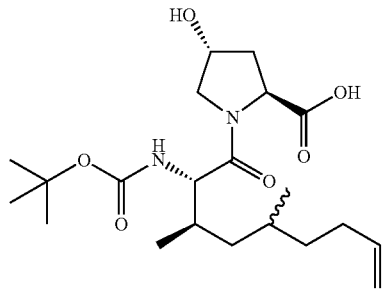 [SMILES: C=CCCC(C)C[C@@H](C)[C@H](NC(=O)OC(C)(C)C)C(=O)N1C[C@H](O)C[C@H]1C(=O)O]

(2S,4R)-methyl 1-((2S,3R)-2-((tert-butoxycarbonyl)amino)-3,5-dimethylnon-8-enoyl)-4-hydroxypyrrolidine-2-carboxylate (10.8 g, 25.3 mmol) was dissolved in THF (50 mL) and MeOH (50 mL) and to this solution was added LiOH (2.425 g, 101 mmol) in Water (50.0 mL). The reaction mixture was stirred at rt for 16 h. The solvent was removed under vacuum and the resulting aqueous residue was diluted with water, and EtOAc. The mixture was neutralized with 1 N HCl and adjusted the pH~2.5 and the mixture was extracted with EtOAc. The organic layer was collected, washed with brine, dried over Na$_2$SO$_4$, and concentrated to give crude (2S,4R)-1-((2S,3R)-2-((tert-butoxycarbonyl)amino)-3,5-dimethyl-non-8-enoyl)-4-hydroxypyrrolidine-2-carboxylic acid (12 g) as yellow viscous oil. MS: MS m/z 413.2 (M$^+$+1).

Step 2: Preparation of tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate

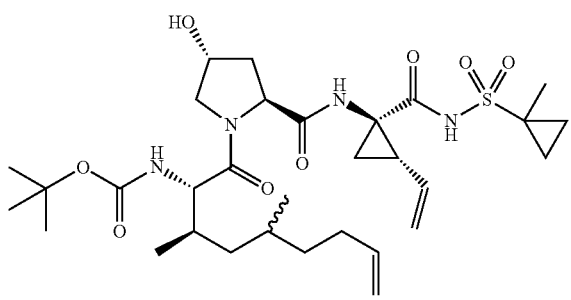 [SMILES: C=CCCC(C)C[C@@H](C)[C@H](NC(=O)OC(C)(C)C)C(=O)N1C[C@H](O)C[C@H]1C(=O)N[C@]1(C(=O)NS(=O)(=O)C2(C)CC2)C[C@H]1C=C]

HATU (7.60 g, 20.00 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (7.86 g, 19.05 mmol), (1R,2S)-1-amino-N-((1-methyl-cyclopropyl)5 sulfonyl)-2-vinylcyclopropanecarboxamide HCl (5.62 g, 20 mmol), and DIPEA (13.31 mL, 76 mmol) in DCM (110 mL). The reaction mixture was stirred at rt for 16 h. The mixture was washed with 1N HCl (3×), and then brine. The organic layer was collected, dried over sodium sulfate, and concentrated under vacuum. The crude material was purified by silica gel chromatography using a gradient of 20-60% Acetone in hexanes. The product fractions were collected and the solvent removed under vacuum to give tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate (9 g, 74% yield) as a light orange foam. MS: MS m/z 639.3 (M$^+$+1).

Step 3: Preparation of tert-butyl((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

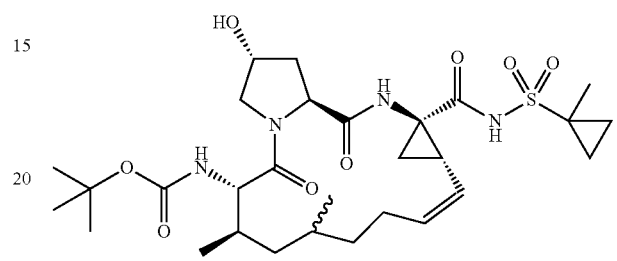

A solution of tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate (8.4 g, 13.15 mmol) in DCE (1500 ml) was degassed with nitrogen for 30 min. and then (1,3-Bis-(2,4,6-trimethylphenyl)-2-imidazolidinylidene) dichloro(o-isopropoxyphenylmethylene)ruthenium) ("Hoveyda-Grubbs Catalyst 2nd Generation", 0.413 g, 0.657 mmol) was added. The reaction solution was heated to 80° C. for 2 h. The reaction solution was concentrated in vacuo the and resulting residue was purified by silica gel chromatography using a gradient of 20-60% Acetone in hexanes to give the mixture of diastereomers tert-butyl((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate as a brown solid (5.6 g, 70% yield). MS: MS m/z 611.3 (M$^+$+1).

Preparation of tert-butyl((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate Scheme

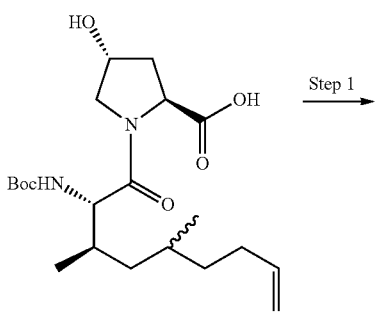

Step 1

31
-continued

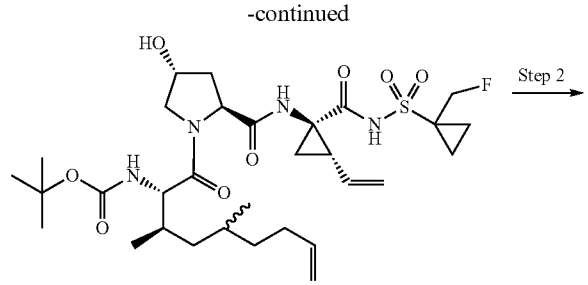

Step 2 →

32
Step 2: Preparation of tert-butyl((2R,6S,7R,13aS, 14aR,16aS,Z)-14a-(((1-(fluoromethyl)cyclopropyl) sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4] diazacyclopentadecin-6-yl)carbamate

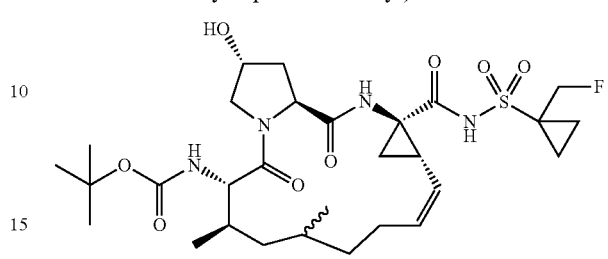

A solution of tert-butyl((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3, 5-dimethyl-1-oxonon-8-en-2-yl)carbamate (7.5 g, 22.84 mmol) in DCE (2855 ml) was spurged with nitrogen for 30 min. and then Hoveyda-Grubbs Catalyst 2nd Generation (0.718 g, 1.142 mmol) was added and the reaction was heated to 80° C. for 2 hrs. The reaction was concentrated and purified by flash chromatography on silica gel (20-60% Acetone in hexanes) to give tert-butyl((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11, 13a,14,14a,15,16,16a-hexadecahydrocyclopropa[e]pyrrolo [1,2-a][1,4]diazacyclopentadecin-6-yl)carbamate (4 g, 6.36 mmol, 27.9% yield). MS: MS m/z 629.3 (M$^+$+1).

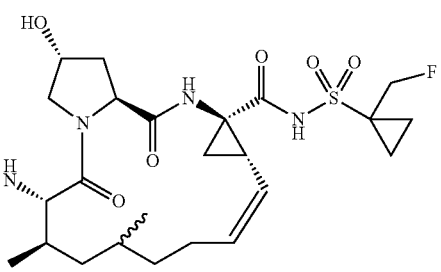

Step 1: Preparation of tert-butyl((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3,5-dimethyl-1-oxonon-8-en-2-yl)carbamate

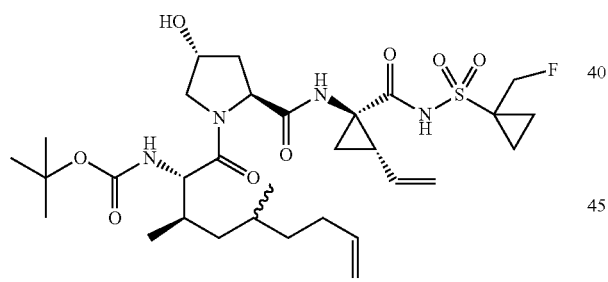

HATU (11.61 g, 30.5 mmol) was added to a DCM (220 mL) solution of (2S,4R)-1-((2S,3R)-2-((tert-butoxycarbonyl)amino)-3,5-dimethylnon-8-enoyl)-4-hydroxypyrrolidine-2-carboxylic acid (10.50 g, 25.5 mmol), (1R,2S)-1-amino-N-((1-(fluoromethyl)cyclopropyl)sulfonyl)-2-vinylcyclopropanecarboxamide HCl (8.37 g, 28 mmol), triethylamine (14.19 mL, 102 mmol). The reaction mixture was stirred at RT for overnight. The reaction was washed with 1N HCl (3×) and then with brine and evaporated on rotovap. The crude material was purified by silica gel chromatography using 20-40% Acetone in hexanes. The product fractions were collected and the solvent removed under vacuum to give the desired product tert-butyl((2S,3R)-1-((2S,4R)-2-(((1R, 2S)-1-(((1-(fluoromethyl)cyclopropyl)sulfonyl)carbamoyl)-2-vinylcyclopropyl)carbamoyl)-4-hydroxypyrrolidin-1-yl)-3,5-dimethyl-1-oxonon-8-en-2-yl)carbamate (15 g, 90% yield). MS: MS m/z 657.3 (M$^+$+1).

Preparation of Compound 1001 and Compound 1002

Compound 1001

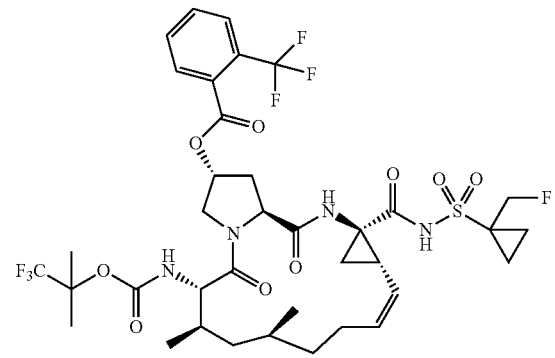

Compound 1002

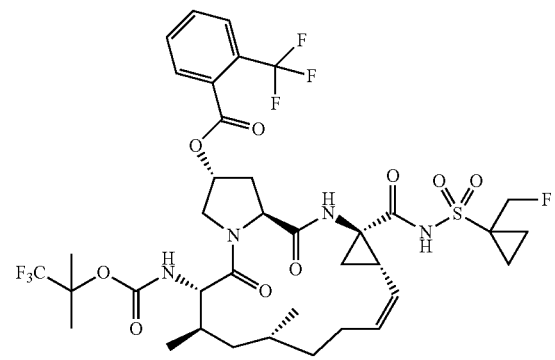

Scheme

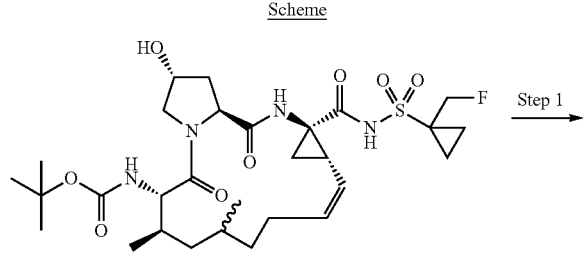

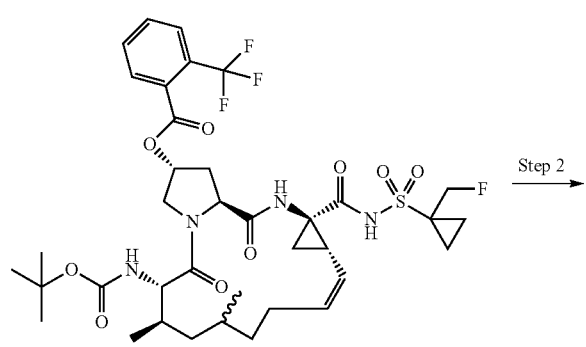

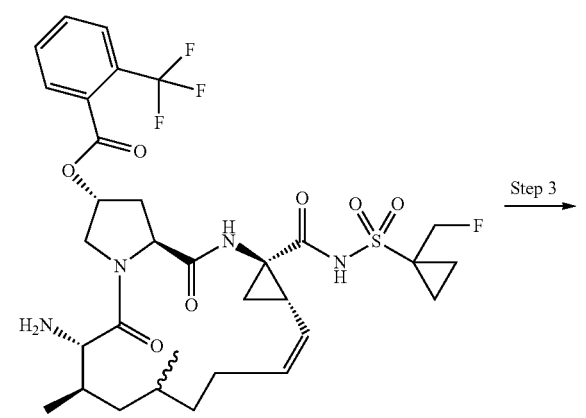

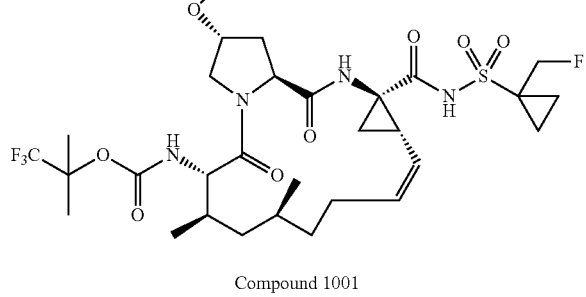

Compound 1001

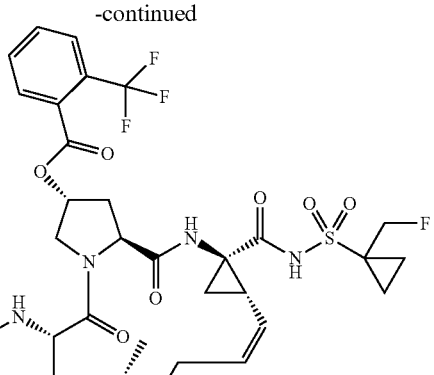

Compound 1002

Step 1

To a mixture of tert-butyl((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (30 mg, 0.048 mmol), 2-(trifluoromethyl)benzoyl chloride (40 mg, 0.19 mmol) in pyridine (1 mL) solution was added DMAP (1.2 mg, 0.001 mmol). The mixture was stirred for 16 h. The mixture was concentrated to give the crude product (2R,6S,7R,9,13aS,14aR,16aS,Z)-6-((tert-butoxycarbonyl)amino)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate that was used in the next step as is. MS: MS m/z 801.4 (M$^+$+1).

Step 2

(2R,6S,7R,9,13aS,14aR,16aS,Z)-6-((tert-butoxycarbonyl)amino)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate (30 mg, 0.04 mmol) was dissolved in DCM (2 mL) and trifluoroacetic acid (TFA, 2 mL) was added. The reaction was stirred for 1 h at room temperature. The volatiles were removed under vacuum to give (2R,6S,7R,13aS,14aR,16aS,Z)-6-amino-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate TFA (26 mg) which was used in the next step as is. MS: MS m/z 701.4 (M$^+$+1).

Step 3

To a solution of (2R,6S,7R,13aS,14aR,16aS,Z)-6-amino-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate TFA (20 mg, 0.03 mmol) and pyridin-2-yl(1,1,1-trifluoro-2-methylpropan-2-yl)carbonate (8.53 mg, 0.034 mmol) in CH$_2$Cl$_2$ (1 mL) was added N-ethyl-N-isopropylpropan-2-amine (Hunig's Base, 0.025 mL, 0.14 mmol). The reaction was stirred for 16 h. The mixture was concentrated and the residue was purified by prep HPLC to give 1.4 mg of Compound 1001 as a solid and 9.1 mg of Compound 1002 as a solid.

Compound 1001: (2R,6S,7R,9S,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate. MS: MS m/z 855.6 (M$^+$+1).

Compound 1002: (2R,6S,7R,9R,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate. $^1$H NMR (500 MHz, DMSO-d$_6$) δ 11.25 (s, 1H), 9.09 (s, 1H), 7.98-7.77 (m, 5H), 5.64 (br. s., 1H), 5.55-5.39 (m, 1H), 5.00 (t, J=9.8 Hz, 1H), 4.39-4.28 (m, 2H), 3.96-3.87 (m, 1H), 3.74 (dd, J=10.7, 8.5 Hz, 1H), 2.62 (q, J=9.3 Hz, 1H), 2.47 (dd, J=14.8, 7.5 Hz, 2H), 2.37-2.23 (m, 2H), 1.86 (dd, J=11.6, 5.8 Hz, 2H), 1.67 (dd, J=12.7, 6.6 Hz, 1H), 1.59-1.49 (m, 7H), 1.41 (br. s., 2H), 1.36 (br. s., 1H), 1.31-1.18 (m, 5H), 1.13 (d, J=12.5 Hz, 1H), 0.90 (d, J=6.1 Hz, 3H), 0.93 (d, J=7.0 Hz, 3H), 0.75 (t, J=12.4 Hz, 1H); MS: MS m/z 855.6 (M$^+$+1).

Preparation of Compound 1003

Compound 1003

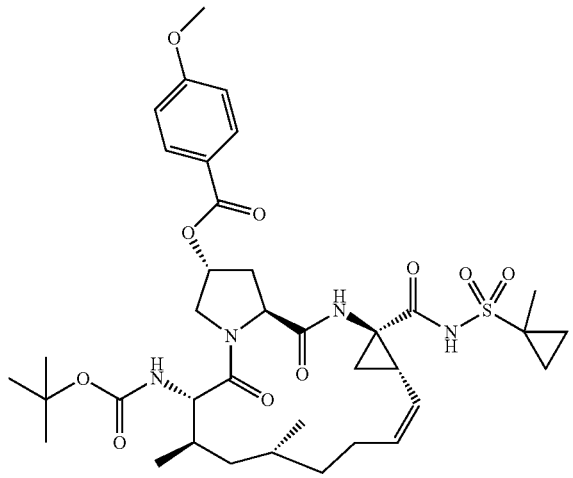

Compounds 1003 was prepared using the intermediates described herein and by following the general procedure described for the synthesis of Compound 1013.

Compound 1003: (2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-methoxybenzoate. $^1$H NMR (500 MHz, METHANOL-d$_4$) δ 8.07-7.84 (m, J=8.5 Hz, 2H), 7.06-6.88 (m, J=8.5 Hz, 2H), 5.69 (d, J=10.1 Hz, 1H), 5.62 (br. s., 1H), 5.13 (t, J=9.5 Hz, 1H), 4.60 (t, J=8.5 Hz, 1H), 4.40 (d, J=11.6 Hz, 1H), 4.16 (d, J=6.7 Hz, 1H), 4.04 (dd, J=11.6, 3.4 Hz, 1H), 3.86 (s, 3H), 2.57 (dd, J=14.0, 7.3 Hz, 2H), 2.47-2.33 (m, 2H), 2.05-1.86 (m, 6H), 1.72 (dd, J=8.2, 5.5 Hz, 1H), 1.66-1.53 (m, 3H), 1.41 (dd, J=9.5, 5.2 Hz, 2H), 1.31 (s, 9H), 1.28-1.20 (m, 2H), 1.10 (d, J=6.7 Hz, 3H), 0.92 (d, J=6.7 Hz, 3H), 0.83 (m, 2H); MS: MS m/z 745.4 (M$^+$+1).

Preparation of Compound 1004 and Compound 1005

Compound 1004

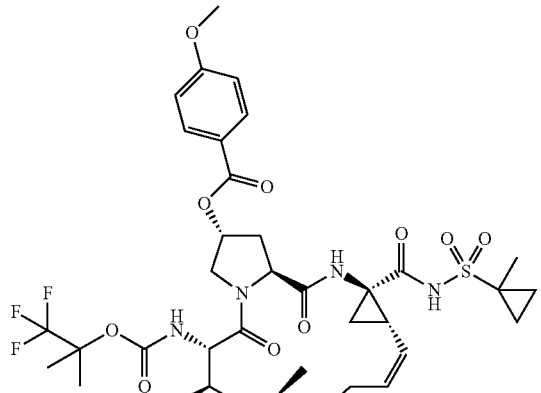

Compound 1005

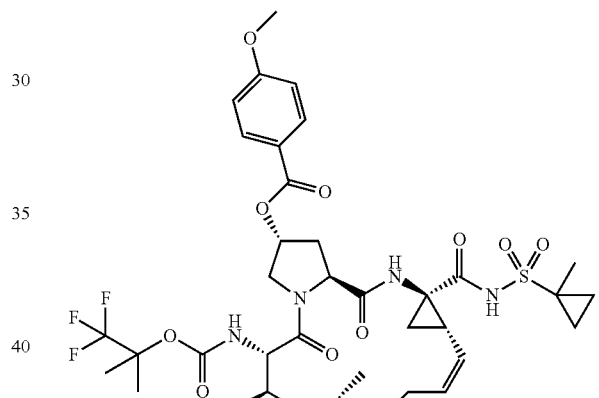

Compounds 1004 and 1005 were prepared using the intermediates described herein and by following the general procedure described for the synthesis of Compounds 1001 and 1002.

Compound 1004: (2R,6S,7R,9S,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-methoxybenzoate. MS: MS m/z 799.0 (M$^+$+1).

Compound 1005: (2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-methoxybenzoate. $^1$H NMR (500 MHz, DMSO-d$_6$) δ 11.02 (s, 1H), 9.16 (br. s., 1H), 7.98-7.80 (m, 3H), 7.03 (d, J=8.9 Hz, 2H), 5.54 (br. s., 2H), 4.97 (t, J=9.8 Hz, 1H), 4.51-4.28 (m, 2H), 3.92-3.81 (m, 5H), 3.70 (dd, J=10.4, 7.9 Hz, 2H), 2.67 (d, J=9.8 Hz, 1H), 2.37-2.18 (m, 3H), 1.90-1.80 (m, 2H), 1.63 (d, J=7.9 Hz, 2H), 1.53

(br. s., 1H), 1.41 (m, 3H), 1.44 (m, 4H), 1.21 (s, 3H), 1.14 (br. s., 2H), 0.92 (dd, J=9.2, 6.7 Hz, 7H), 0.75 (t, J=12.7 Hz, 2H); MS: MS m/z 799.0 (M$^+$+1).

Preparation of Compound 1006

Compound 1006

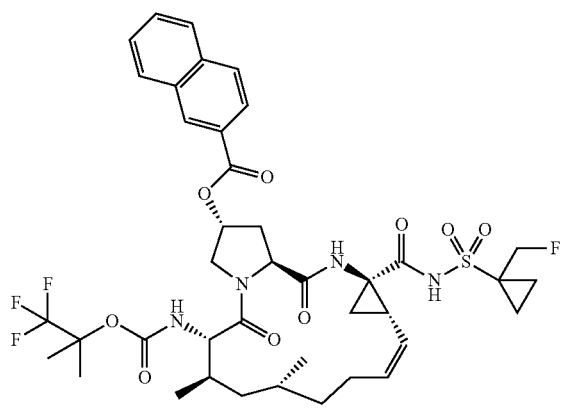

Compound 1006 was prepared using the intermediates described herein and by following the general procedure described for the synthesis of Compound 1002.

Compound 1006: (2R,6S,7R,9R,13aS,14aR,16aS,Z)-14a-((((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-naphthoate. $^1$H NMR (400 MHz, METHANOL-d$_4$) δ 8.59 (s, 1H), 8.11-7.87 (m, 4H), 7.67-7.42 (m, 2H), 5.70 (t, J=3.3 Hz, 1H), 5.59 (td, J=10.1, 5.9 Hz, 1H), 5.09 (br. s., 1H), 4.88 (d, J=11.0 Hz, 1H), 4.71-4.58 (m, 3H), 4.53 (d, J=11.0 Hz, 1H), 4.00 (dd, J=11.8, 3.3 Hz, 1H), 3.82 (d, J=10.8 Hz, 1H), 2.72-2.60 (m, 2H), 2.50-2.31 (m, 2H), 2.00-1.75 (m, 3H), 1.74-1.54 (m, 3H), 1.51-1.38 (m, 2H), 1.32 (s, 3H), 1.26-1.09 (m, 3H), 0.99 (d, J=6.3 Hz, 3H), 1.00 (d, J=6.8 Hz, 3H), 0.86 (s, 3H), 0.83-0.77 (m, 1H); MS: MS m/z 837.4 (M$^+$+1).

Preparation of Compound 1007 and Compound 1008

Compound 1007

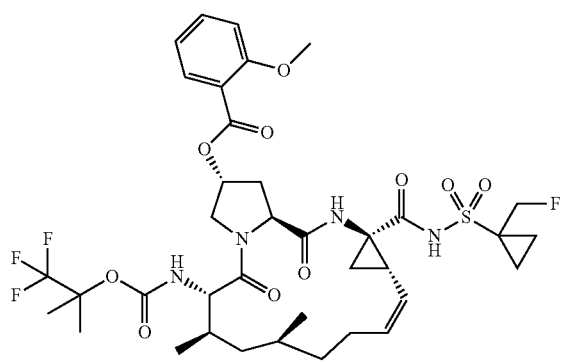

Compound 1008

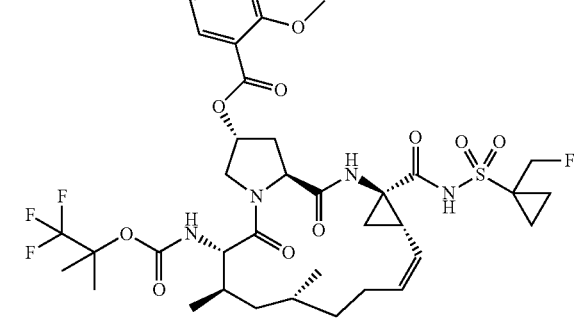

Compounds 1007 and 1008 were prepared using the intermediates described herein and by following the general procedure described for the synthesis of Compounds 1001 and 1002.

Compound 1007: (2R,6S,7R,9S,13aS,14aR,16aS,Z)-14a-((((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-methoxybenzoate. MS: MS m/z 817.6 (M$^+$+1).

Compound 1008: (2R,6S,7R,9R,13aS,14aR,16aS,Z)-14a-((((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-methoxybenzoate. $^1$H NMR (500 MHz, DMSO-d$_6$) δ 11.27 (s, 1H), 9.09 (s, 1H), 7.88 (d, J=8.2 Hz, 1H), 7.66 (dd, J=7.8, 1.7 Hz, 1H), 7.59-7.52 (m, 1H), 7.16 (d, J=8.2 Hz, 1H), 6.99 (t, J=7.5 Hz, 1H), 5.53 (br. s., 2H), 5.04-4.97 (m, 2H), 4.86 (d, J=11.6 Hz, 1H), 4.59 (d, J=11.3 Hz, 1H), 4.50 (d, J=11.3 Hz, 1H), 4.41 (dd, J=10.2, 6.9 Hz, 1H), 4.33 (d, J=11.3 Hz, 1H), 3.87 (dd, J=11.6, 3.4 Hz, 1H), 3.82 (s, 3H), 3.73 (dd, J=10.7, 8.2 Hz, 1H), 2.65 (q, J=9.2 Hz, 1H), 2.45 (dd, J=13.9, 7.2 Hz, 1H), 2.34-2.21 (m, 2H), 1.95-1.76 (m, 2H), 1.67 (dd, J=12.8, 7.0 Hz, 1H), 1.61-1.51 (m, 4H), 1.49 (s, 3H), 1.42 (d, J=12.5 Hz, 1H), 1.39-1.34 (m, 1H), 1.30-1.20 (m, 5H), 1.19-1.10 (m, 1H), 0.90 (d, J=6.4 Hz, 3H), 0.93 (d, J=6.7 Hz, 2H), 0.82-0.69 (m, 1H); MS: MS m/z 817.6 (M$^+$+1).

Preparation of Compound 1009 and Compound 1010

Compound 1009

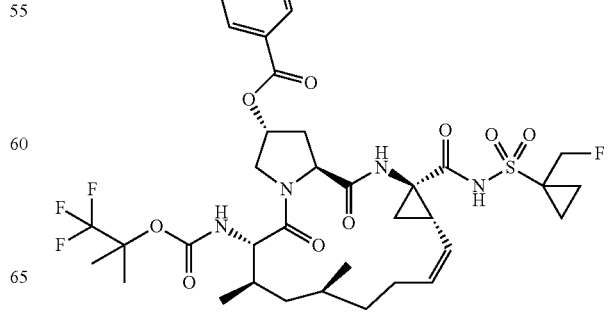

-continued

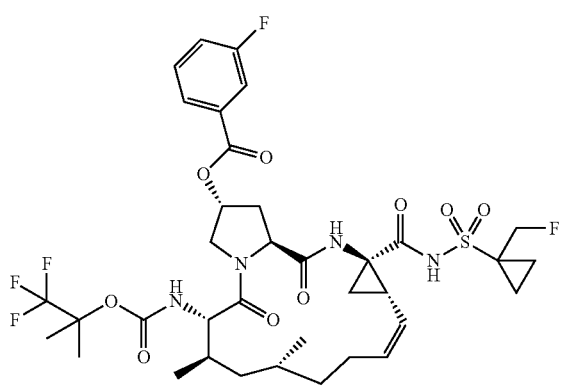
Compound 1010

Compounds 1009 and 1010 were prepared using the intermediates described herein and by following the general procedure described for the synthesis of Compounds 1001 and 1002.

Compound 1009: (2R,6S,7R,9S,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 3-fluorobenzoate. MS: MS m/z 805.6 (M$^+$+1).

Compound 1010: (2R,6S,7R,9R,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 3-fluorobenzoate. $^1$H NMR (500 MHz, DMSO-d$_6$) δ 11.26 (s, 1H), 9.08 (br. s., 1H), 7.89 (d, J=7.3 Hz, 1H), 7.82 (d, J=7.3 Hz, 1H), 7.68-7.53 (m, 4H), 5.58 (br. s., 1H), 5.51 (br. s., 1H), 5.00 (t, J=9.5 Hz, 1H), 4.85 (d, J=11.3 Hz, 1H), 4.75 (d, J=11.3 Hz, 1H), 4.60 (d, J=11.6 Hz, 1H), 4.55-4.36 (m, 3H), 3.86 (d, J=9.8 Hz, 1H), 3.68 (dd, J=10.7, 7.6 Hz, 1H), 2.66-2.57 (m, 1H), 2.30 (t, J=10.1 Hz, 2H), 1.83 (d, J=7.0 Hz, 2H), 1.67 (br. s., 1H), 1.55 (m, 3H), 1.42 (s, 3H), 1.25 (d, J=12.8 Hz, 2H), 1.18 (s, 3H), 0.92 (m, 8H), 0.80-0.67 (m, 1H); MS: MS m/z 805.6 (M$^+$+1).

Preparation of Compound 1011

Compound 1011

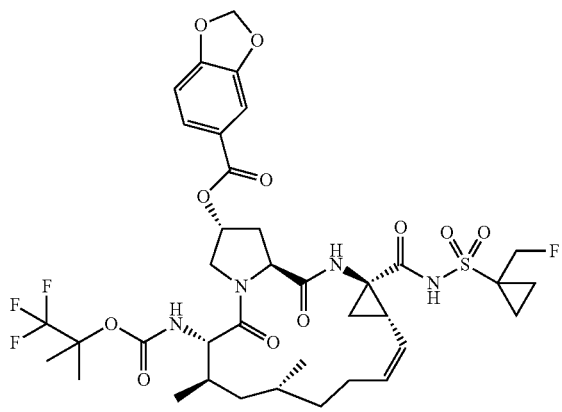

Compound 1011 was prepared using the intermediates described herein and by following the general procedure described for the synthesis of Compound 1002.

Compound 1011: (2R,6S,7R,9R,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl benzo[d][1,3]dioxole-5-carboxylate. $^1$H NMR (500 MHz, DMSO-d$_6$) δ 11.25 (s, 1H), 9.06 (s, 1H), 7.88 (d, J=7.6 Hz, 1H), 7.57 (dd, J=8.1, 1.7 Hz, 1H), 7.37 (d, J=1.5 Hz, 1H), 7.04 (d, J=7.9 Hz, 1H), 6.14 (d, J=4.0 Hz, 2H), 5.52 (br. s., 2H), 5.00 (t, J=9.9 Hz, 1H), 4.59 (d, J=11.6 Hz, 1H), 4.46-4.37 (m, 2H), 3.83 (d, J=8.5 Hz, 1H), 3.69 (dd, J=10.7, 7.6 Hz, 1H), 2.64 (d, J=9.8 Hz, 1H), 2.47 (m, 1H), 2.36-2.23 (m, 2H), 1.89-1.81 (m, 2H), 1.68 (m, 1H), 1.61-1.50 (m, 4H), 1.47 (s, 3H), 1.42 (m, 2H), 1.39-1.33 (m, 1H), 1.28 (m, 5H), 1.14 (d, J=12.5 Hz, 1H), 0.91 (d, J=9.5 Hz, 3H), 0.93 (d, J=10.1 Hz, 3H), 0.75 (t, J=12.2 Hz, 1H); MS: MS m/z 831.5 (M$^+$+1).

Preparation of Compound 1012 and Compound 1013

Compound 1012

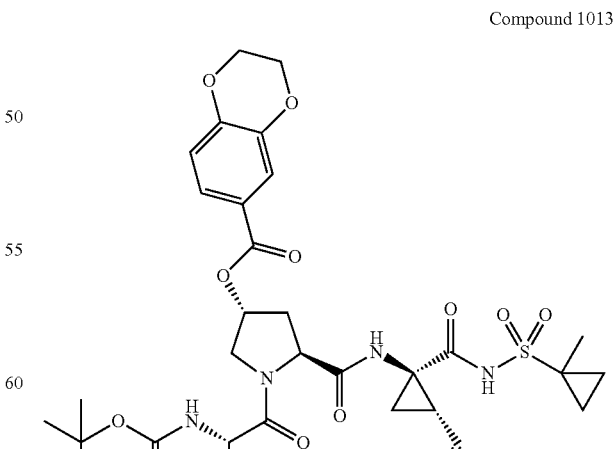

Compound 1013

Scheme

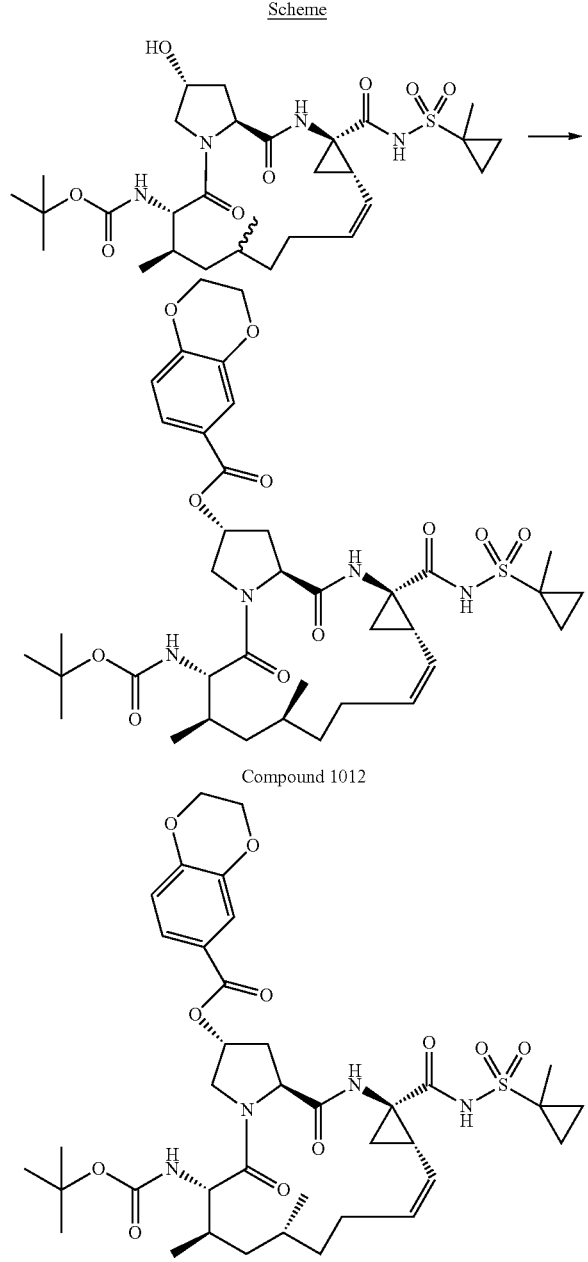

Compound 1012

Compound 1013

Step

To a mixture of tert-butyl((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (40 mg, 0.065 mmol), 2,3-dihydrobenzo[b][1,4]dioxine-6-carbonyl chloride (52.0 mg, 0.262 mmol) in pyridine (1 mL) solution was added DMAP (4 mg, 0.033 mmol). The mixture was stirred for 16 h. The mixture was concentrated and the residue was purified by prep HPLC to give 6.2 mg of Compound 1012 as a solid and 26.5 mg of Compound 1013 as a solid.
Compound 1012: (2R,6S,7R,9S,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 2,3-dihydrobenzo[b][1,4]dioxine-6-carboxylate. MS: MS m/z 773.7 (M⁺+1).
Compound 1013: (2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 2,3-dihydrobenzo[b][1,4]dioxine-6-carboxylate. $^1$H NMR (500 MHz, DMSO-$d_6$) δ 11.25 (s, 1H), 8.96 (br. s., 1H), 7.45 (d, J=8.5 Hz, 1H), 7.37 (br. s., 1H), 7.17 (d, J=7.3 Hz, 1H), 6.91 (d, J=8.2 Hz, 1H), 5.49 (m, 2H), 5.06 (m, 1H), 4.50-4.37 (m, 2H), 4.31 (m, 2H), 4.26 (m, 3H), 3.81 (d, J=11.9 Hz, 1H), 3.69-3.61 (m, 1H), 2.59 (m, 1H), 2.42 (m, 1H), 2.33-2.18 (m, 3H), 1.91 (m, 2H), 1.87 (m, 1H), 1.77 (d, J=11.6 Hz, 1H), 1.65 (m, 1H), 1.57 (m, 1H), 1.45 (m, 2H), 1.38 (m, 6H), 1.25 (m, 2H), 1.17 (m, 6H), 0.89 (m, 6H), 0.70 (t, J=12.2 Hz, 1H); MS: MS m/z 773.7 (M⁺+1).

Preparation of Compound 1014 and Compound 1015

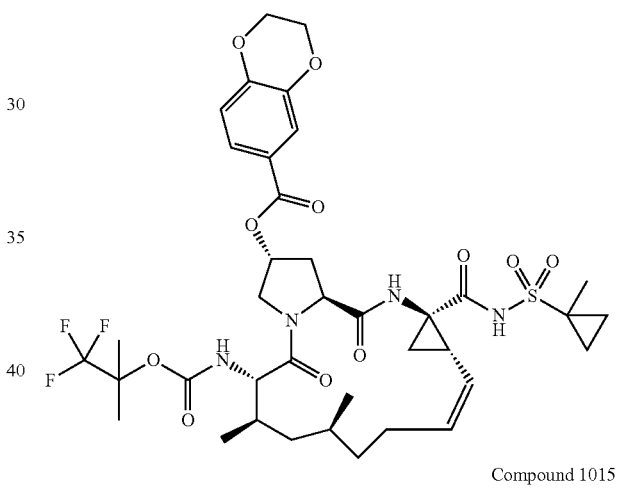

Compound 1014

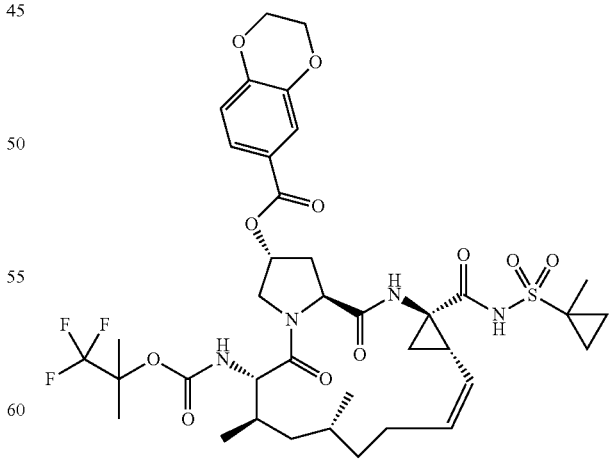

Compound 1015

Compounds 1014 and 1015 were prepared using the intermediates described herein and by following the general procedure described for the synthesis of Compounds 1001 and 1002.

Compound 1014: (2R,6S,7R,9S,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2,3-dihydrobenzo[b][1,4]dioxine-6-carboxylate. MS: MS m/z 827.6 (M$^+$+1).

Compound 1015: (2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2,3-dihydrobenzo[b][1,4]dioxine-6-carboxylate. MS: MS m/z 827.6 (M$^+$+1).

Preparation of Compound 1301 and Compound 1302

Compound 1301

Compound 1302

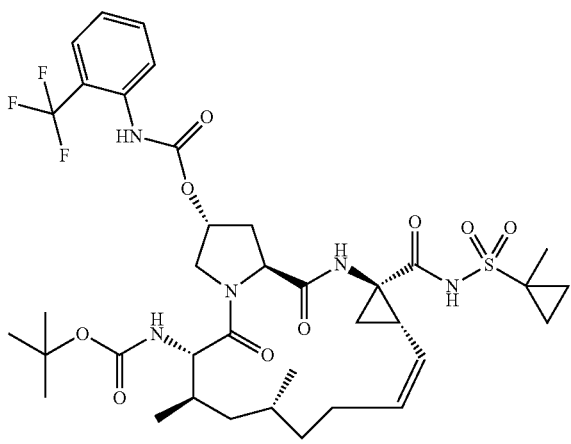

Scheme

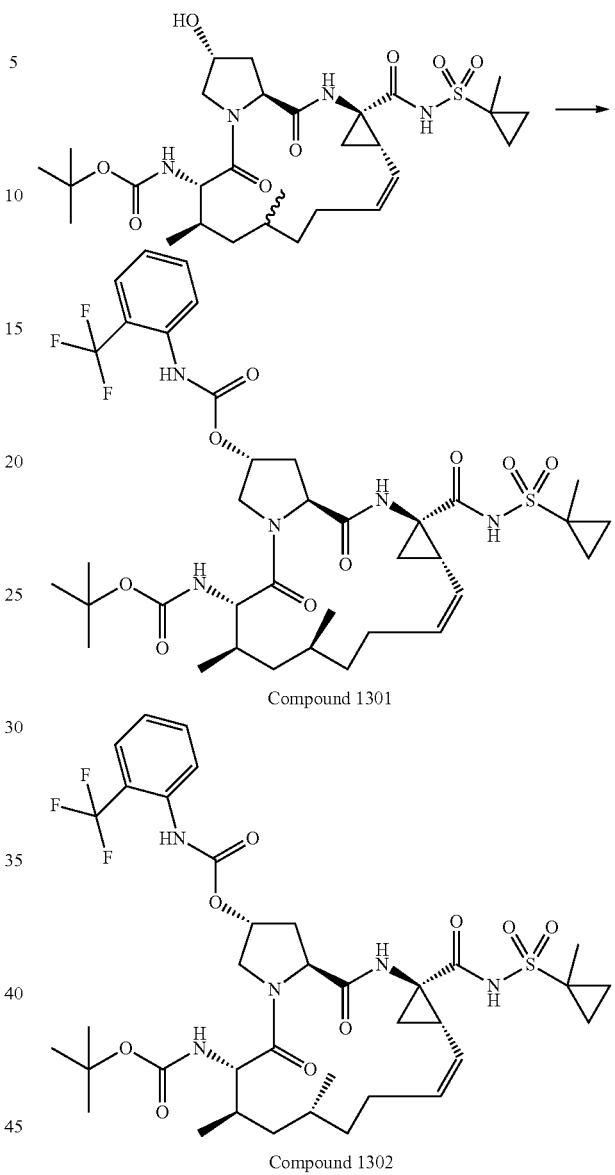

A solution (2R,6S,7R,9S,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(2-(trifluoromethyl)phenyl)carbamate (14.8 mg, 0.019 mmol, 18.55% yield), 1-isocyanato-2-(trifluoromethyl)benzene (37.4 mg, 0.2 mmol) and Et$_3$N (0.042 mL, 0.3 mmol) in CH$_2$Cl$_2$ (1 mL) was stirred for 16 h. After concentration, the residue was purified by prep HPLC to 14.8 mg of Compound 1301 and 23 mg of Compound 1302, respectively.

Compound 1301: (2R,6S,7R,9S,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(2-(trifluoromethyl)phenyl)carbamate. MS: MS m/z 798.7 (M$^+$+1).

Compound 1302: (2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(2-(trifluoromethyl)phenyl)carbamate. MS: MS m/z 798.7 (M⁺+1).

Preparation of Compound 1303 and Compound 1304

[e]pyrrolo[1,2-a][1,4]diazacyclopentadecin-2-yl(4-fluorophenyl)carbamate. MS: MS m/z 748.7 (M⁺+1).

Preparation of Compound 1305 and Compound 1306

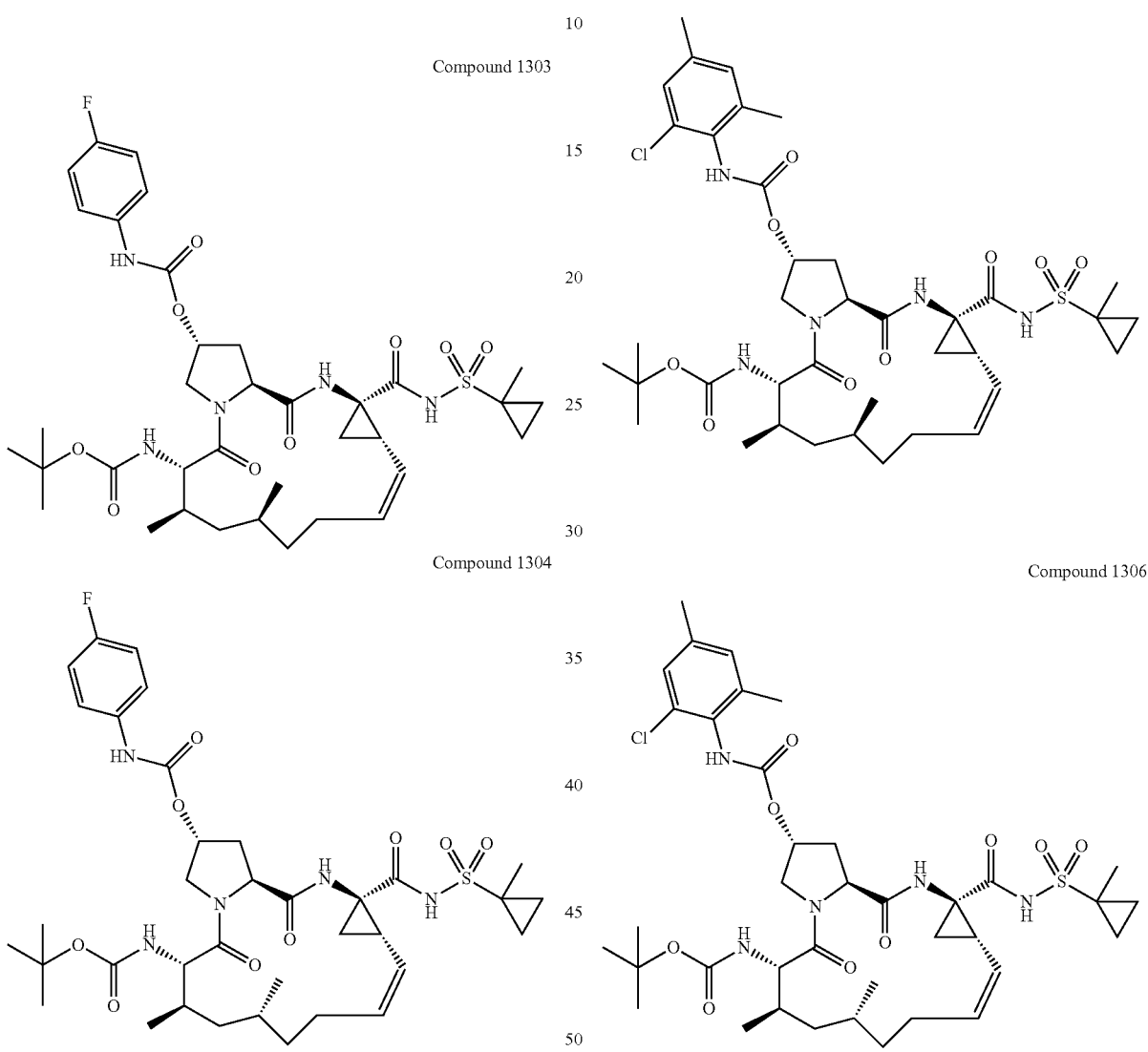

Compounds 1303 and 1304 were prepared using the intermediates described herein and by following the general procedure described for the synthesis of Compounds 1301 and 1302.

Compound 1303: (2R,6S,7R,9S,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate. MS: MS m/z 748.7 (M⁺+1).

Compound 1304: (2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa Compounds 1305 and 1306 were prepared using the intermediates described herein and by following the general procedure described for the synthesis of Compounds 1301 and 1302.

Compound 1305: (2R,6S,7R,9S,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(2-chloro-4,6-dimethylphenyl)carbamate. MS: MS m/z 792.7 (M⁺+1).

Compound 1306: (2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa

[e]pyrrolo[1,2-a][1,4]diazacyclopentadecin-2-yl(2-chloro-4,6-dimethylphenyl)carbamate. MS: MS m/z 792.8 (M⁺+1).

Preparation of Compound 1307

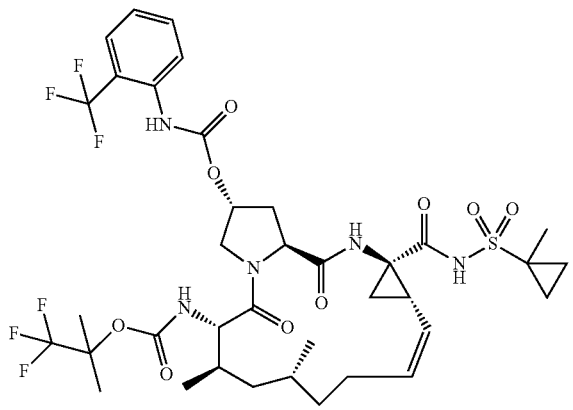
Compound 1307

Compound 1307 was prepared using the intermediates described herein and by following the general procedure described for the synthesis of Compounds 1308 and 1309.
Compound 1307: (2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl(2-(trifluoromethyl)phenyl)carbamate. MS: MS m/z 852.8 (M⁺+1).

Preparation of Compound 1308 and Compound 1309

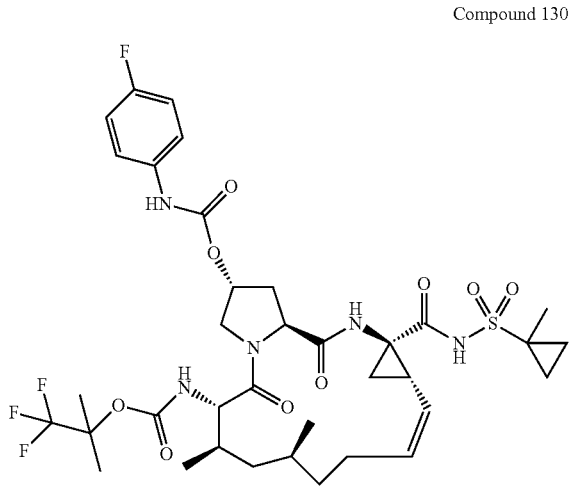
Compound 1308

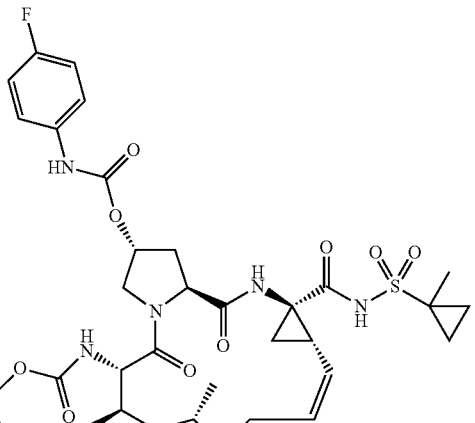
Compound 1309

Scheme

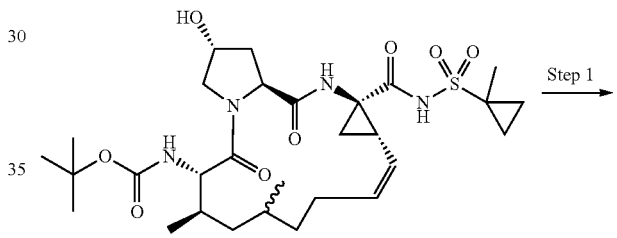
Step 1

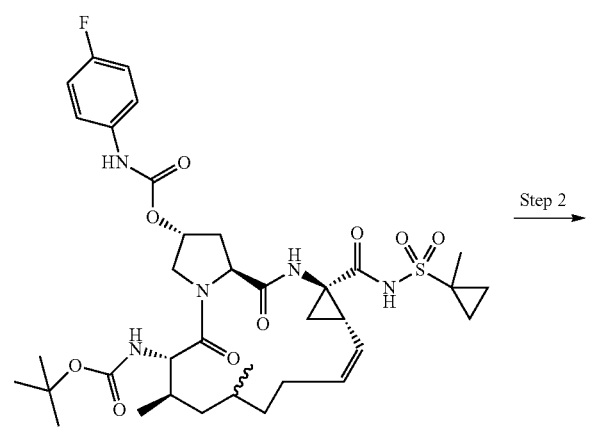
Step 2

49
-continued

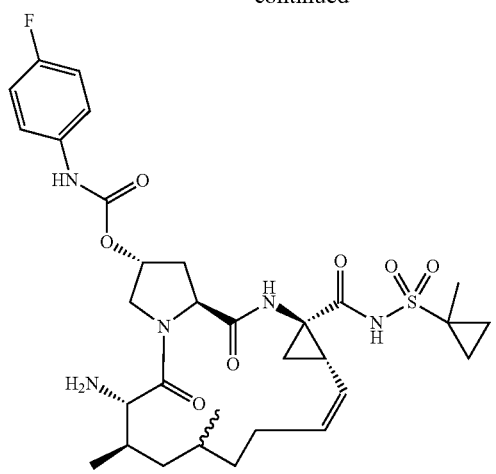

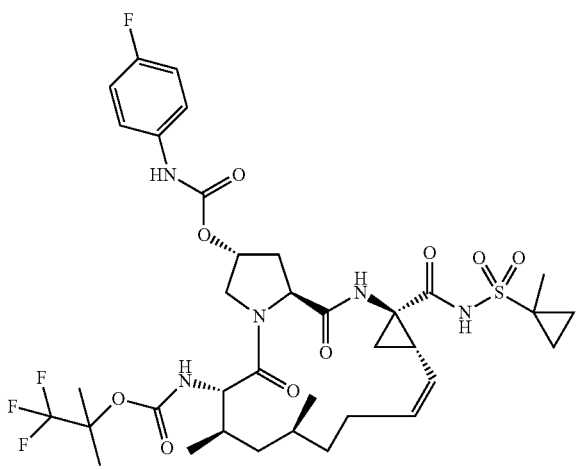
Compound 1308

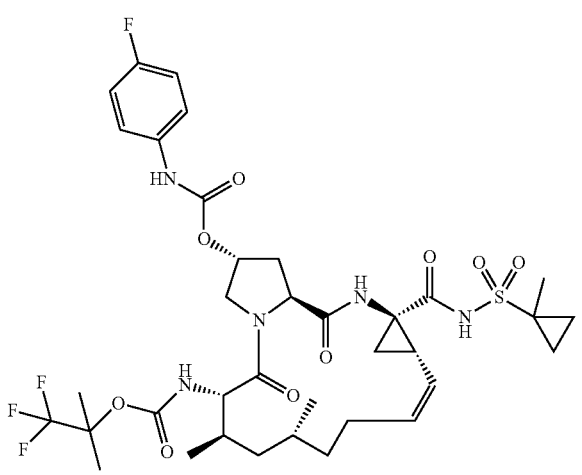
Compound 1309

50

Step 1

A solution (2R,6S,7R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate (112 mg, 0.150 mmol, 100% yield), 1-fluoro-4-isocyanatobenzene (20.57 mg, 0.15 mmol) and $Et_3N$ (0.042 mL, 0.3 mmol) in DCM (1 mL) was stirred for 16 h. Concentration gave 122 mg of a crude product (2R,6S,7R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate, which was used in the next step as it was.

Step 2

To a solution of (2R,6S,7R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate (37.4 mg, 0.05 mmol) in $CH_2Cl_2$ (1 mL) was added TFA (0.039 mL, 0.500 mmol). After stirring for 1 h, concentration gave 38 mg of a crude product as TFA salt (2R,6S,7R,13aS,14aR,16aS,Z)-6-amino-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate, TFA, that was used in the next step as it is. MS: MS m/z 648.3 ($M^+$+1).

Step 3

A solution of (2R,6S,7R,13aS,14aR,16aS,Z)-6-amino-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate, TFA (76 mg, 0.1 mmol), pyridin-2-yl(1,1,1-trifluoro-2-methylpropan-2-yl)carbonate (29.9 mg, 0.120 mmol), and N-ethyl-N-isopropylpropan-2-amine (0.087 mL, 0.500 mmol) in $CH_2Cl_2$ (1 mL) was stirred for 16 h. After concentration, the residue was purified by prep HPLC to 25.3 mg of Compound 1308 as a solid and 22.4 mg of Compound 1309 as a solid.

Compound 1308: (2R,6S,7R,9S,13aS,14aR,16aS,Z)-7,9-dimethyl-14a-(((1-methylcyclopropyl)sulfonyl)carbamoyl)-5,16-dioxo-6-(((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate. MS: MS m/z 802.7 ($M^+$+1).

Compound 1309: (2R,6S,7R,9R,13aS,14aR,16aS,Z)-7,9-dimethyl-14a-(((1-methylcyclopropyl)sulfonyl)carbamoyl)-5,16-dioxo-6-(((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl(4-fluorophenyl)carbamate. MS: MS m/z 802.8 ($M^+$+1).

Preparation of Compound 1310 and Compound 1311

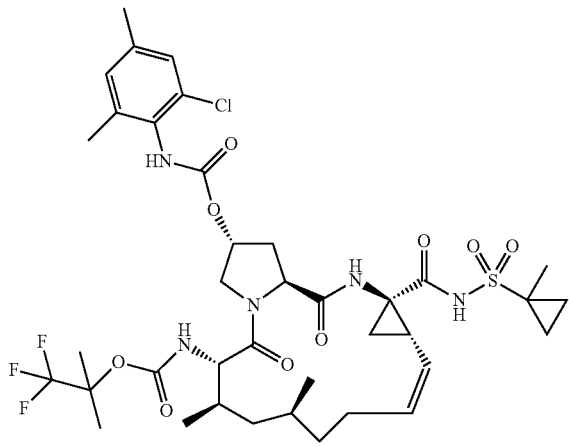

Compound 1310

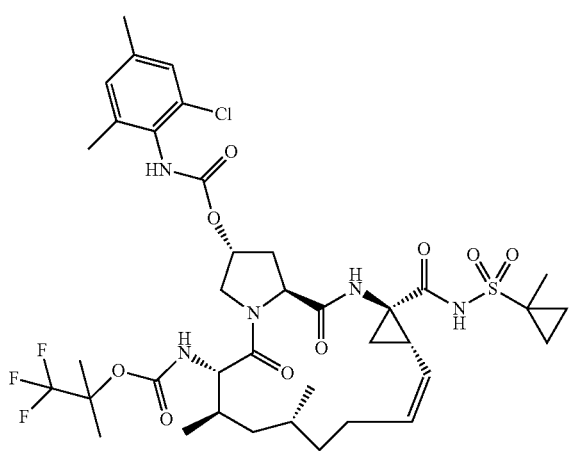

Compound 1311

Compound 1310 and Compound 1311 were prepared using the intermediates described herein and by following the general procedure described for the synthesis of Compounds 1308 and 1309.

Compound 1310: (2R,6S,7R,9S,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl)(2-chloro-4,6-dimethylphenyl)carbamate. MS: MS m/z 846.9 ($M^+$+1).

Compound 1311: (2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl)(2-chloro-4,6-dimethylphenyl)carbamate. MS: MS m/z 846.8 ($M^+$+1).

Preparation of Compound 1312 and Compound 1313

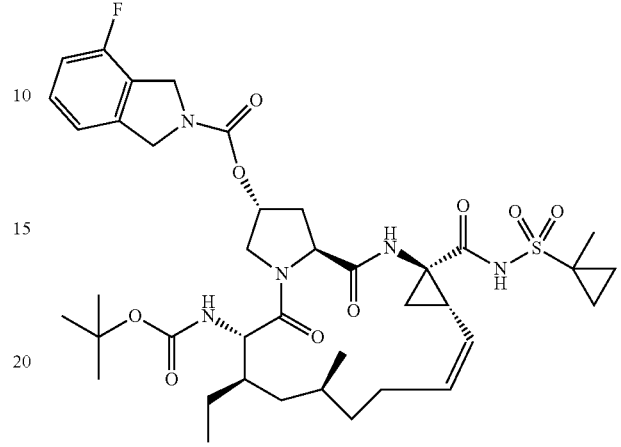

Compound 1312

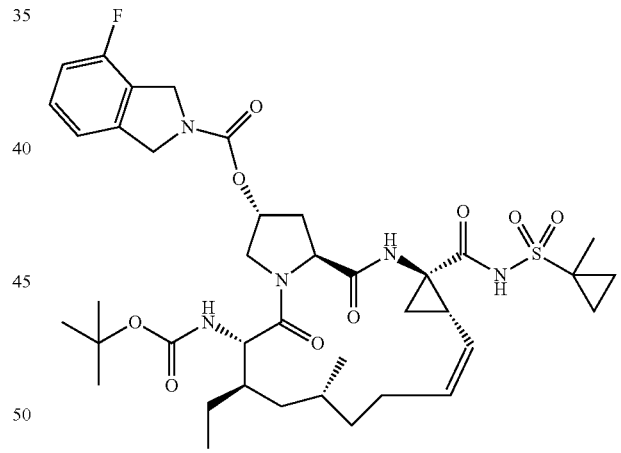

Compound 1313

Scheme

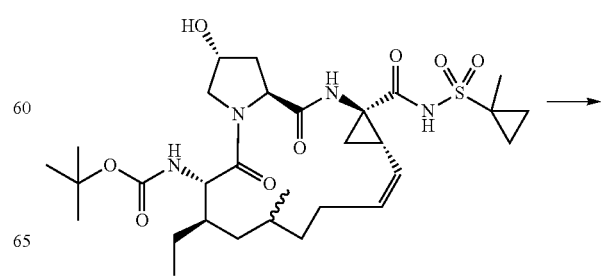

Preparation of Compound 1314 and Compound 1315

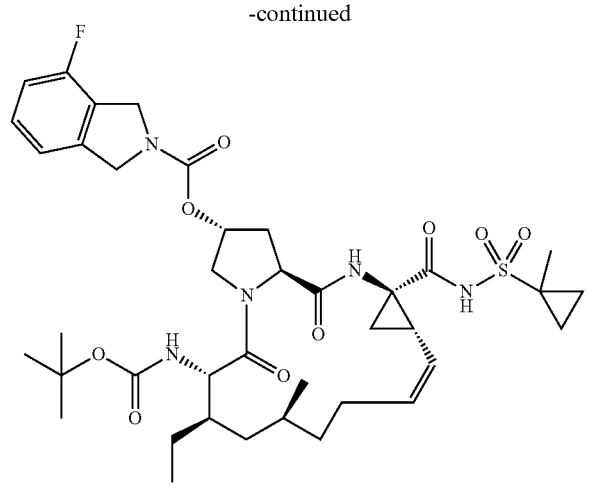

Compound 1312

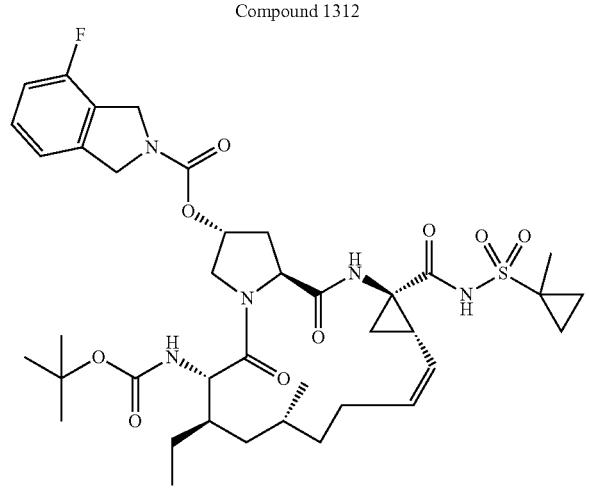

Compound 1313

A solution of tert-butyl(((2R,6S,7R,13aS,14aR,16aS,Z)-7-ethyl-2-hydroxy-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (37.5 mg, 0.06 mmol) and CDI (11.67 mg, 0.072 mmol) was stirred for 6 h. To the solution was added 4-fluoroisoindoline (10.70 mg, 0.078 mmol), and then stirred overnight. After concentration, the residue was purified by prep HPLC to 10 mg of Compound 1312 as a solid and 22.9 mg of Compound 1313 as a solid, respectively.

Compound 1312: (2R,6S,7R,9S,13aS,14aR,16aS,Z)-6-((tert-butoxycarbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 786.7 (M$^+$−1).

Compound 1313: (2R,6S,7R,9R,13aS,14aR,16aS,Z)-6-((tert-butoxycarbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 786.7 (M$^+$−1).

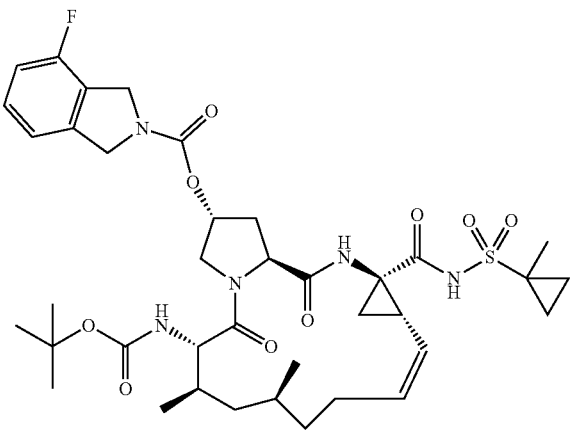

Compound 1314

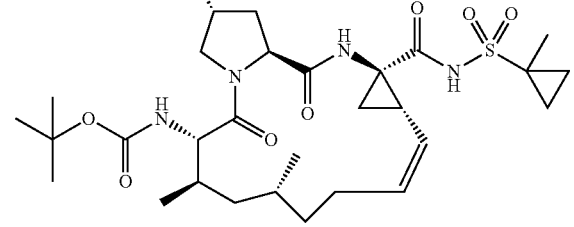

Compound 1315

Compound 1314 and Compound 1315 were prepared using the intermediates described herein and by following the general procedure described for the synthesis of Compounds 1312 and 1313.

Compound 1314: (2R,6S,7R,9S,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 774.5 (M$^+$+1).

Compound 1315: (2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 774.6 (M$^+$+1).

Preparation of Compound 1316 and Compound 1317

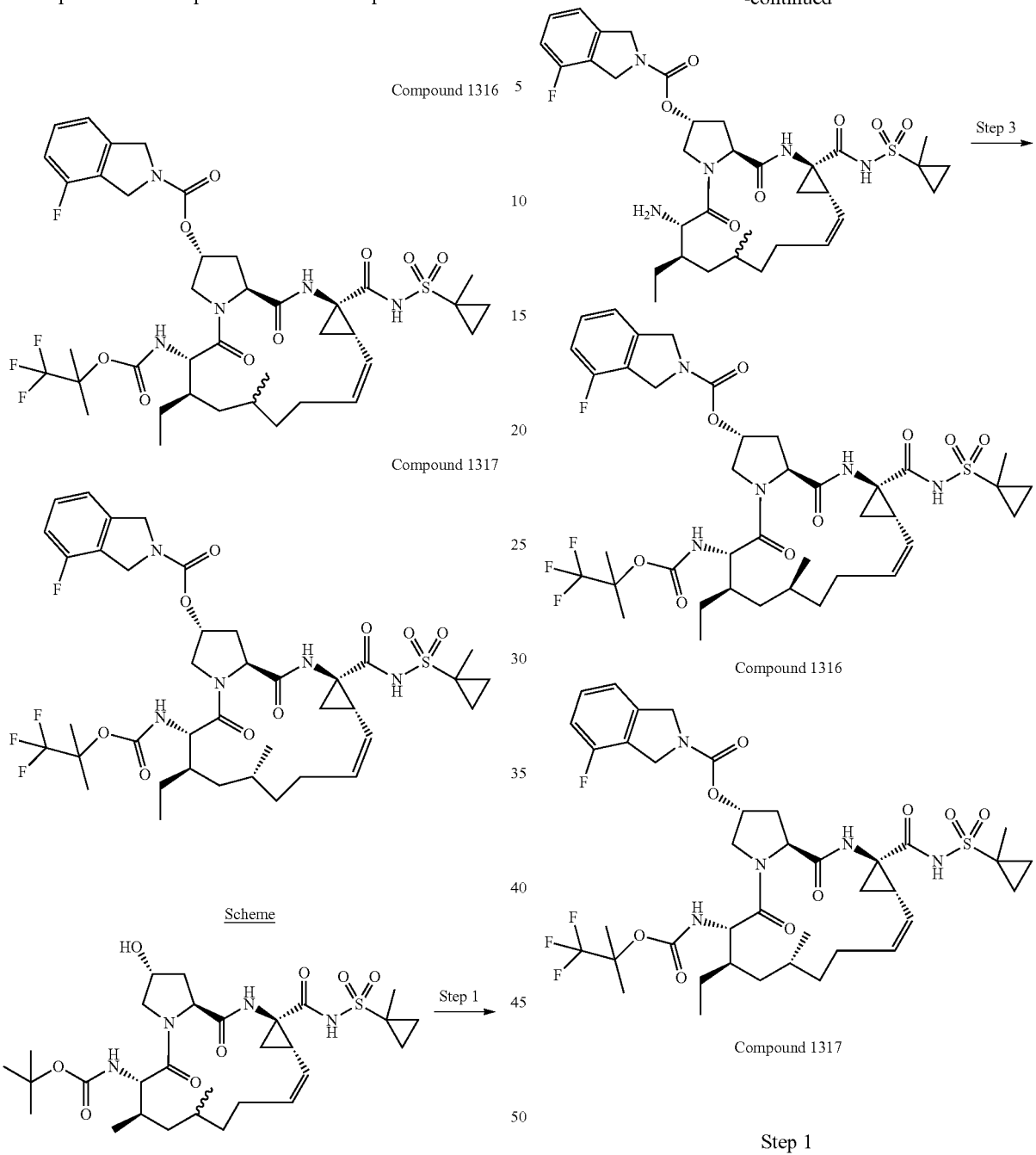

Step 1

A solution of tert-butyl((2R,6S,7R,13aS,14aR,16aS,Z)-7-ethyl-2-hydroxy-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (0.062 g, 0.1 mmol) and CDI (0.019 g, 0.120 mmol) was stirred for 6 h. To the solution was added 4-fluoroisoindoline (0.018 g, 0.130 mmol), and then stirred overnight. Concentration gave 80 mg of a crude mixtures (2R,6S,7R,13aS,14aR,16aS,Z)-6-((tert-butoxycarbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate, which was used as it was.

Step 2

To a solution of (2R,6S,7R,13aS,14aR,16aS,Z)-6-((tert-butoxycarbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate (126 mg, 0.16 mmol) in CH2Cl2 (1 mL) was added TFA (0.123 mL, 1.600 mmol). After stirring for 1 h, concentration gave 128 mg of a crude product as TFA salt, (2R,6S,7R,13aS,14aR,16aS,Z)-6-amino-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate, TFA, which was used in the next step as it is.

Step 3

A solution of (2R,6S,7R,13aS,14aR,16aS,Z)-6-amino-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate, TFA (55.1 mg, 0.07 mmol), pyridin-2-yl(1,1,1-trifluoro-2-methylpropan-2-yl)carbonate (20.93 mg, 0.084 mmol), and N-ethyl-N-isopropylpropan-2-amine (0.061 mL, 0.350 mmol) in $CH_2Cl_2$ (1 mL) was stirred for 16 h. After concentration, the residue was purified by prep HPLC to give 23 mg of Compound 1316 as a solid and 20.6 mg of Compound 1617 as a solid, respectively.

Compound 1316: (2R,6S,7R,9S,13aS,14aR,16aS,Z)-7-ethyl-9-methyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 840.7 (M$^+$+1).

Compound 1317: (2R,6S,7R,9R,13aS,14aR,16aS,Z)-7-ethyl-9-methyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 840.7 (M$^+$−1).

Preparation of Compound 1318 and Compound 1319

Compound 1318

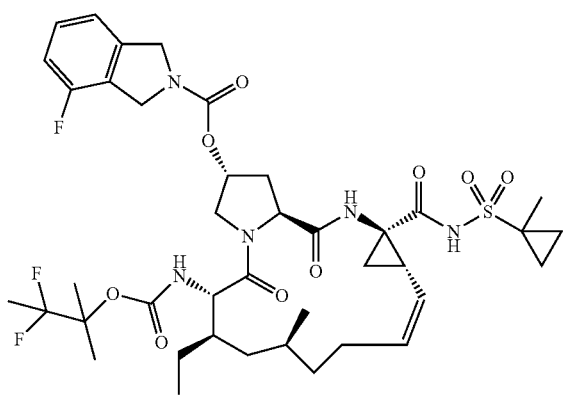

Compound 1319

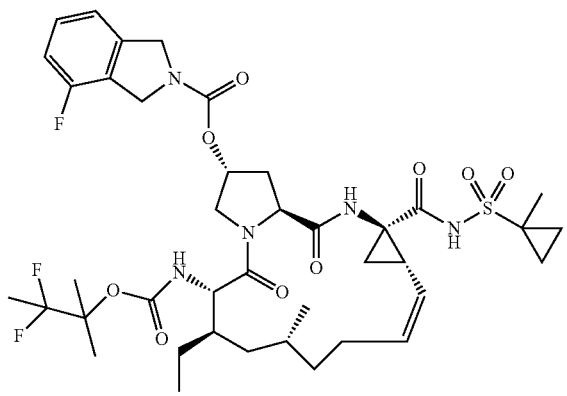

Compound 1318 and Compound 1319 were prepared using the intermediates described herein and by following the general procedure described for the synthesis of Compounds 1316 and 1317.

Compound 1318: (2R,6S,7R,9S,13aS,14aR,16aS,Z)-6-((((3,3-difluoro-2-methylbutan-2-yl)oxy)carbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 836.7 (M$^+$−1).

Compound 1319: (2R,6S,7R,9R,13aS,14aR,16aS,Z)-6-((((3,3-difluoro-2-methylbutan-2-yl)oxy)carbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 836.7 (M$^+$−1).

Preparation of Compound 1320 and Compound 1321

Compound 1320

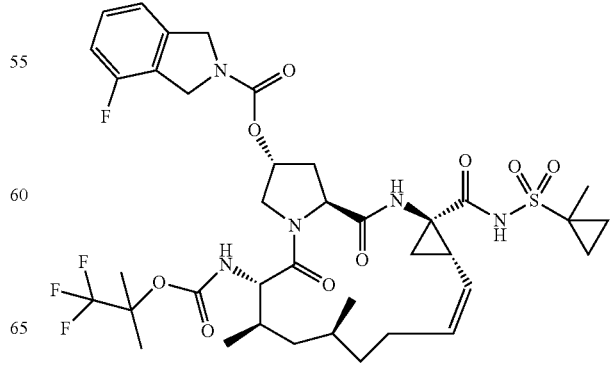

Compound 1321

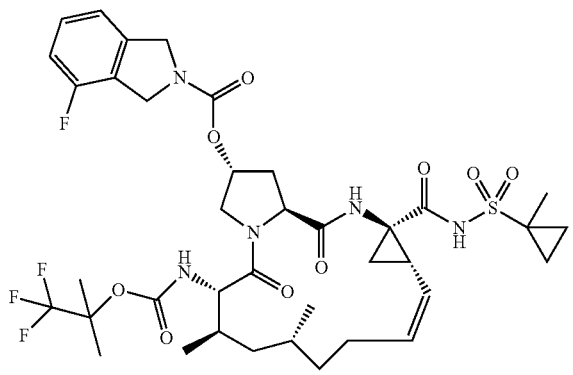

Compound 1320 and Compound 1321 were prepared using the intermediates described herein and by following the general procedure described for the synthesis of Compounds 1316 and 1317.

Compound 1320: (2R,6S,7R,9S,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 826.6 (M$^+$−1).

Compound 1321: (2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 826.6 (M$^+$−1).

Preparation of Compound 1322 and Compound 1323

Compound 1322

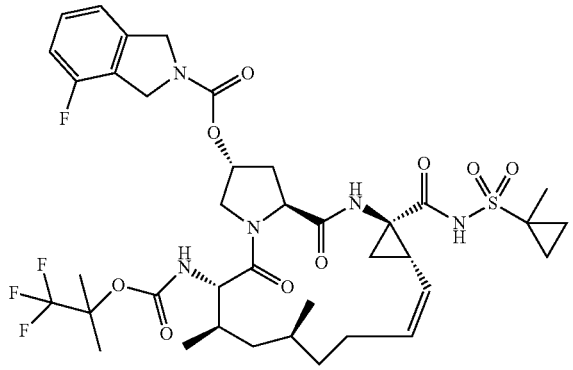

Compound 1323

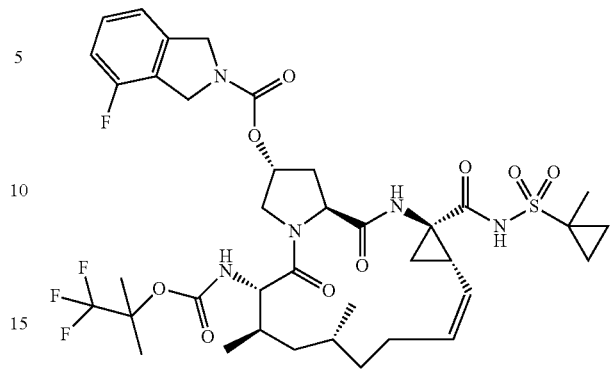

Compound 1322 and Compound 1323 were prepared using the intermediates described herein and by following the general procedure described for the synthesis of Compounds 1316 and 1317.

Compound 1322: (2R,6S,7R,9S,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 822.7 (M$^+$−1).

Compound 1323: (2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate. MS: MS m/z 822.7 (M$^+$−1).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams of wet cell paste. The cells were resuspended in lysis buffer (10 mL/gram) consisting of 25 mM N-(2-Hydroxyethyl)Piperazine-N'-(2-Ethane Sulfonic acid) (HEPES) pH 7.5, 20% glycerol, 500 mM Sodium Chloride (NaCl), 0.5% Triton X-100, 1 microgram/milliliter ("µg/mL") lysozyme, 5 mM Magnesium Chloride ($MgCl_2$), 1 µg/ml DnaseI, 5 mM β-Mercaptoethanol (βME), Protease inhibitor-Ethylenediamine Tetraacetic acid (EDTA)free (Roche). The mixture was homogenized and incubated for 20 minutes (min) at 4° C. The homogenate was sonicated and clarified by ultra-centrifugation at 235,000 g for 1 hour (h) at 4° C. Imidazole was added to the supernatant to a final concentration of 15 mM and the pH was adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer E (25 mM HEPES, pH 7.5, 20% glycerol, 300 mM NaCl, 0.2% Triton X-100, 10 mM βME). Sample was loaded and eluted with buffer E at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^D)))$.

Compounds of the present disclosure, which were tested against more than one type of NS3/4A complex, were found to have similar inhibitory properties though the compounds uniformly demonstrated greater potency against the 1b strains as compared to the 1a strains.

Generation of HCV Replicon

An HCV GT1b(Con1) replicon cell system was established as described by Lohmann V, Korner F, Koch J, Herian U, Theilmann L, Bartenschlager R., Science 285(5424):110-3 (1999) and modified to introduce a luciferase reporter (Krieger N, Lohmann V, and Bartenschlager R, *J. Virol.* 75(10):4614-4624 (2001)). cDNA encoding a humanized form of the Renilla luciferase gene, and a linker sequence fused directly to the 3'-end of the luciferase gene were introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated by first linearizing plasmid DNAs with ScaI. RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV GT1a(H77) replicon luciferase reporter cell line (Yanagi M, Purcell R H, Emerson S U, et al. Transcripts from a single full-length cDNA clone of hepatitis C virus are infectious when directly transfected into the liver of a chimpanzee. Proc Natl Acad Sci USA 1997; 94(16):8738-8743) was generated as described previously for the genotype 1b(Con1) replicon luciferase cell line. The replicon construct was modified by introducing mutations into the genes encoding the NS3 helicase domain (proline replaced by leucine at position 1496) and NS5A (serine to isoleucine at position 2204) to improve replication in cell culture.

HCV Replicon Luciferase Reporter Assay

HCV replicon luciferase assays were developed to monitor the inhibitory effects of compounds described in the disclosure on HCV genotypes 1a and 1b viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 µL of cells at a density of $3.0 \times 10^3$ cells/well in DMEM containing 4% FCS (final DMSO concentration at 0.5%). After 3 days incubation at 37° C., cells were analyzed for Renilla Luciferase activity using the EnduRen as substrate (Promega cat #E6485). The EnduRen substrate was diluted in DMEM and then added to the plates to a final concentration of 7.5 µM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat # G8082). Cell-Titer Blue (3 µL) was added to each well and incubated for 8 hrs at 37° C. The fluorescence signal from each well was read, with an excitation wavelength at 525/10 nm and an emission wavelength of 598/10 nm, using the Viewlux Imager.

The $EC_{50}$ values for compounds were calculated by using a four-parameter logistic equation:

$$y = A + ((B-A)/(1+((C/x)^D)))),$$

where A and B denotes minimal and maximal % inhibition, respectively, C is the $EC_{50}$, D is the hill slope and x represents compound concentration.

Table 2 shows the $EC_{50}$ values of representative compounds of the present disclosure. Ranges are as follows: A=0.10 nM-0.50 nM; B=0.51 nM-1.00 nM; C=1.01 nM-5.00 nM; D=5.01 nM-35.00 nM; and E=35.01 nM-62.5 nM.

TABLE 2

| Compound Number | LE_1a (EC50, nM) | LE_1a (EC50, range) | LE_1b (EC50, nM) | LE_1b (EC50, range) |
| --- | --- | --- | --- | --- |
| 1002 | | D | | C |
| 1003 | | D | | D |
| 1005 | 1.15 | C | 0.75 | B |
| 1006 | | C | | C |
| 1008 | | D | | C |
| 1010 | | D | | C |
| 1011 | 7.98 | D | 1.68 | C |
| 1012 | | D | | C |
| 1013 | | C | | C |
| 1015 | | D | | C |
| 1302 | | D | | C |
| 1304 | 62.47 | E | 20.61 | D |
| 1306 | | D | | D |
| 1307 | | C | | C |
| 1309 | | E | | D |
| 1311 | | E | | D |
| 1312 | | D | | C |
| 1313 | | C | | C |
| 1314 | | D | | C |
| 1315 | 0.96 | B | 0.33 | A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

[Chemical structure of formula (I)]

or a pharmaceutically acceptable salt thereof, wherein
p is 1 or 2;
----- is a single or double bond;
R¹ is selected from aryl and —NR$^q$R$^{q'}$, wherein R$^q$ and R$^{q'}$ are independently selected from hydrogen, alkyl, and phenyl wherein the phenyl is optionally fused to a five- or six-membered heterocyclic ring containing two oxygen atoms and wherein the phenyl is optionally substituted with one, two, or three groups independently selected from alkoxy, alkyl, halo, and haloalkyl; or, wherein R$^q$ and R$^{q'}$, together with the nitrogen atom to which they are attached, form a five membered ring optionally fused to a phenyl ring, wherein the phenyl ring is optionally substituted with one, two, or three groups independently selected from alkoxy, alkyl, halo, and haloalkyl;
R$^x$ is selected from methyl and ethyl;
R$^y$ and R$^z$ are independently selected from hydrogen and hydroxy; provided that when ----- is a double bond, R$^y$ and R$^z$ are each hydrogen;
R² is selected from hydrogen, alkyl, halo, haloalkoxy, haloalkyl, and hydroxyalkyl; and
R³ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl.

2. A compound of claim 1, or a pharmaceutically acceptable salt thereof, wherein m is 1.

3. A compound of claim 2, or a pharmaceutically acceptable salt thereof, wherein ----- is a double bond.

4. A compound of claim 1, or a pharmaceutically acceptable salt thereof, wherein p is 1.

5. A compound of claim 1, or a pharmaceutically acceptable salt thereof, wherein R² is selected from alkyl and haloalkyl.

6. A compound of claim 1, or a pharmaceutically acceptable salt thereof, wherein R³ is selected from alkoxycarbony and haloalkoxycarbonyl.

7. A compound of claim 1, or a pharmaceutically acceptable salt thereof, wherein:
m is 1,
----- is a double bond;
p is 1;
R² is selected from alkyl and haloalkyl; and
R³ is selected from alkoxycarbony and haloalkoxycarbonyl.

8. A compound selected from
(2R,6S,7R,9S,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate;
(2R,6S,7R,9R,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-(trifluoromethyl)benzoate;
(2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-methoxybenzoate;
(2R,6S,7R,9S,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-methoxybenzoate;
(2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-methoxybenzoate;
(2R,6S,7R,9R,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-naphthoate;
(2R,6S,7R,9S,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-methoxybenzoate;
(2R,6S,7R,9R,13aS,14aR,16aS,Z)-14a-(((1-(fluoromethyl)cyclopropyl)sulfonyl)carbamoyl)-7,9-dimethyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 2-methoxybenzoate;
(2R,6S,7R,9S,13aS,14aR,16aS,Z)-14a-(((1-(fluoromethyl)cyclopropyl)sulfonyl)carbamoyl)-7,9-dimethyl- 5,16-dioxo-6-((((1,1,1-trifluoro-2-methylpropan-2-yl)
oxy)carbonyl)amino)-1,2,3,5,6,7,8,9,10,11,13a,14,14a,
15,16,16a-hexadecahydrocyclopropa[e]pyrrolo[1,2-a]
[1,4]diazacyclopentadecin-2-yl 3-fluorobenzoate;

(2R,6S,7R,9R,13aS,14aR,16aS,Z)-14a-(((1-(fluorom-
ethyl)cyclopropyl)sulfonyl)carbamoyl)-7,9-dimethyl-
5,16-dioxo-6-((((1,1,1-trifluoro-2-methylpropan-2-yl)
oxy)carbonyl)amino)-1,2,3,5,6,7,8,9,10,11,13a,14,14a,
15,16,16a-hexadecahydrocyclopropa[e]pyrrolo[1,2-a]
[1,4]diazacyclopentadecin-2-yl 3-fluorobenzoate;

(2R,6S,7R,9R,13aS,14aR,16aS,Z)-14a-(((1-(fluorom-
ethyl)cyclopropyl)sulfonyl)carbamoyl)-7,9-dimethyl-
5,16-dioxo-6-((((1,1,1-trifluoro-2-methylpropan-2-yl)
oxy)carbonyl)amino)-1,2,3,5,6,7,8,9,10,11,13a,14,14a,
15,16,16a-hexadecahydrocyclopropa[e]pyrrolo[1,2-a]
[1,4]diazacyclopentadecin-2-yl benzo[d][1,3]dioxole-
5-carboxylate;

(2R,6S,7R,9S,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl 2,3-
dihydrobenzo[b][1,4]dioxine-6-carboxylate;

(2R,6S,7R,9R,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl 2,3-
dihydrobenzo[b][1,4]dioxine-6-carboxylate;

(2R,6S,7R,9S,13aS,14aR,16aS,Z)-7,9-dimethyl-14a-(((1-
methylcyclopropyl)sulfonyl)carbamoyl)-5,16-dioxo-6-
((((1,1,1-trifluoro-2-methylpropan-2-yl)oxy)carbonyl)
amino)-1,2,3,5,6,7,8,9,10,11,13a,14,14a,15,16,16a-
hexadecahydrocyclopropa[e]pyrrolo[1,2-a][1,4]
diazacyclopentadecin-2-yl 2,3-dihydrobenzo[b][1,4]
dioxine-6-carboxylate;

(2R,6S,7R,9R,13aS,14aR,16aS,Z)-7,9-dimethyl-14a-
(((1-methylcyclopropyl)sulfonyl)carbamoyl)-5,16-di-
oxo-6-((((1,1,1-trifluoro-2-methylpropan-2-yl)oxy)
carbonyl)amino)-1,2,3,5,6,7,8,9,10,11,13a,14,14a,15,
16,16a-hexadecahydrocyclopropa[e]pyrrolo[1,2-a][1,
4]diazacyclopentadecin-2-yl 2,3-dihydrobenzo[b][1,4]
dioxine-6-carboxylate;

(2R,6S,7R,9S,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl(2-
(trifluoromethyl)phenyl)carbamate;

(2R,6S,7R,9R,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl(2-
(trifluoromethyl)phenyl)carbamate;

(2R,6S,7R,9S,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl(4-
fluorophenyl)carbamate;

(2R,6S,7R,9R,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl(4-
fluorophenyl)carbamate;

(2R,6S,7R,9S,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl(2-
chloro-4,6-dimethylphenyl)carbamate;

(2R,6S,7R,9R,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl(2-
chloro-4,6-dimethylphenyl)carbamate;

(2R,6S,7R,9R,13aS,14aR,16aS,Z)-7,9-dimethyl-14a-
(((1-methylcyclopropyl)sulfonyl)carbamoyl)-5,16-di-
oxo-6-((((1,1,1-trifluoro-2-methylpropan-2-yl)oxy)
carbonyl)amino)-1,2,3,5,6,7,8,9,10,11,13a,14,14a,15,
16,16a-hexadecahydrocyclopropa[e]pyrrolo[1,2-a][1,
4]diazacyclopentadecin-2-yl(2-(trifluoromethyl)
phenyl)carbamate;

(2R,6S,7R,9S,13aS,14aR,16aS,Z)-7,9-dimethyl-14a-(((1-
methylcyclopropyl)sulfonyl)carbamoyl)-5,16-dioxo-6-
((((1,1,1-trifluoro-2-methylpropan-2-yl)oxy)carbonyl)
amino)-1,2,3,5,6,7,8,9,10,11,13a,14,14a,15,16,16a-
hexadecahydrocyclopropa[e]pyrrolo[1,2-a][1,4]
diazacyclopentadecin-2-yl(4-fluorophenyl)carbamate;

(2R,6S,7R,9R,13aS,14aR,16aS,Z)-7,9-dimethyl-14a-
(((1-methylcyclopropyl)sulfonyl)carbamoyl)-5,16-di-
oxo-6-((((1,1,1-trifluoro-2-methylpropan-2-yl)oxy)
carbonyl)amino)-1,2,3,5,6,7,8,9,10,11,13a,14,14a,15,
16,16a-hexadecahydrocyclopropa[e]pyrrolo[1,2-a][1,
4]diazacyclopentadecin-2-yl(4-fluorophenyl)
carbamate;

(2R,6S,7R,9S,13aS,14aR,16aS,Z)-7,9-dimethyl-14a-(((1-
methylcyclopropyl)sulfonyl)carbamoyl)-5,16-dioxo-6-
((((1,1,1-trifluoro-2-methylpropan-2-yl)oxy)carbonyl)
amino)-1,2,3,5,6,7,8,9,10,11,13a,14,14a,15,16,16a-
hexadecahydrocyclopropa[e]pyrrolo[1,2-a][1,4]
diazacyclopentadecin-2-yl(2-chloro-4,6-
dimethylphenyl)carbamate;

(2R,6S,7R,9R,13aS,14aR,16aS,Z)-7,9-dimethyl-14a-
(((1-methylcyclopropyl)sulfonyl)carbamoyl)-5,16-di-
oxo-6-((((1,1,1-trifluoro-2-methylpropan-2-yl)oxy)
carbonyl)amino)-1,2,3,5,6,7,8,9,10,11,13a,14,14a,15,
16,16a-hexadecahydrocyclopropa[e]pyrrolo[1,2-a][1,
4]diazacyclopentadecin-2-yl(2-chloro-4,6-
dimethylphenyl)carbamate;

(2R,6S,7R,9S,13aS,14aR,16aS,Z)-6-((tert-butoxycarbo-
nyl)amino)-7-ethyl-9-methyl-14a-(((1-methylcyclo-
propyl)sulfonyl)carbamoyl)-5,16-dioxo-1,2,3,5,6,7,8,
9,10,11,13a,14,14a,15,16,16a-
hexadecahydrocyclopropa[e]pyrrolo[1,2-a][1,4]
diazacyclopentadecin-2-yl 4-fluoroisoindoline-2-
carboxylate;

(2R,6S,7R,9R,13aS,14aR,16aS,Z)-6-((tert-butoxycarbo-
nyl)amino)-7-ethyl-9-methyl-14a-(((1-methylcyclo-
propyl)sulfonyl)carbamoyl)-5,16-dioxo-1,2,3,5,6,7,8,
9,10,11,13a,14,14a,15,16,16a-
hexadecahydrocyclopropa[e]pyrrolo[1,2-a][1,4]
diazacyclopentadecin-2-yl 4-fluoroisoindoline-2-
carboxylate;

(2R,6S,7R,9S,13aS,14aR,16aS,Z)-6-((tert-butoxycarbo-
nyl)amino)-7,9-dimethyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-2-yl
4-fluoroisoindoline-2-carboxylate;

(2R,6S,7R,9R,13aS,14aR,16aS,Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate;

(2R,6S,7R,9S,13aS,14aR,16aS,Z)-7-ethyl-9-methyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate;

(2R,6S,7R,9R,13aS,14aR,16aS,Z)-7-ethyl-9-methyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate;

(2R,6S,7R,9S,13aS,14aR,16aS,Z)-6-((((3,3-difluoro-2-methylbutan-2-yl)oxy)carbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate;

(2R,6S,7R,9R,13aS,14aR,16aS,Z)-6-((((3,3-difluoro-2-methylbutan-2-yl)oxy)carbonyl)amino)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate;

(2R,6S,7R,9S,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate;

(2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate; and (2R,6S,7R,9R,13aS,14aR,16aS,Z)-7,9-dimethyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate;

or a pharmaceutically acceptable salt thereof.

9. A composition comprising a compound of formula (I), or a pharmaceutically acceptable salt thereof, and a pharmaceutically acceptable carrier.

10. The composition of claim 9 further comprising at least one additional compound having anti-HCV activity.

11. The composition of claim 10 wherein at least one of the additional compounds is an interferon or a ribavirin.

12. The composition of claim 11 wherein the interferon is selected from interferon alpha 2B, pegylated interferon alpha, pegylated interferon lambda, consensus interferon, interferon alpha 2A, and lymphoblastiod interferon tau.

13. The composition of claim 10 wherein at least one of the additional compounds is selected from interleukin 2, interleukin 6, interleukin 12, Imiquimod, ribavirin, an inosine 5'-monophosphate dehydrogenase inhibitor, amantadine, and rimantadine.

14. The composition of claim 10 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

15. A method of treating an HCV infection in a patient, comprising administering to the patient a therapeutically effective amount of a compound of formula (I), or a pharmaceutically acceptable salt thereof.

16. The method of claim 15 further comprising administering at least one additional compound having anti-HCV activity prior to, after, or simultaneously with the compound of formula (I), or a pharmaceutically acceptable salt thereof.

17. The method of claim 13 wherein at least one of the additional compounds is an interferon or a ribavirin.

18. The method of claim 17 wherein the interferon is selected from interferon alpha 2B, pegylated interferon alpha, pegylated interferon lambda, consensus interferon, interferon alpha 2A, and lymphoblastiod interferon tau.

19. The method of claim 16 wherein at least one of the additional compounds is selected from interleukin 2, interleukin 6, interleukin 12, Imiquimod, ribavirin, an inosine 5'-monophosphate dehydrogenase inhibitor, amantadine, and rimantadine.

20. The method of claim 16 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *